US010787439B2

(12) United States Patent
Golden et al.

(10) Patent No.: US 10,787,439 B2
(45) Date of Patent: Sep. 29, 2020

(54) COMPOUNDS AND METHODS FOR ACTIVATING THE APOPTOTIC ARM OF THE UNFOLDED PROTEIN RESPONSE

(71) Applicants: University of Kansas, Lawrence, KS (US); The Regents of the University of Michigan, Ann Arbor, MI (US); Wayne State University, Detroit, MI (US); Sanford-Burnham Medical Research Institute, La Jolla, CA (US)

(72) Inventors: Jennifer E. Golden, Olathe, KS (US); Jeffrey Aube, Lawrence, KS (US); Daniel P. Flaherty, Overland Park, KS (US); Andrew M. Fribley, Brighton, MI (US); Randal J. Kaufman, San Diego, CA (US); Thomas D. Y. Chung, Carlsbad, CA (US); Anthony B. Pinkerton, San Diego, CA (US); Michael Pablo Hedrick, Carlsbad, CA (US)

(73) Assignees: UNIVERSITY OF KANSAS, Lawrence, KS (US); THE REGENTS OF THE UNIVERSITY OF MICHIGAN, Ann Arbor, MI (US); SANFORD-BURNHAM MEDICAL RESEARCH INSTITUTE, La Jolla, CA (US); WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 15/672,574

(22) Filed: Aug. 9, 2017

(65) Prior Publication Data
US 2017/0334889 A1 Nov. 23, 2017

Related U.S. Application Data

(62) Division of application No. 14/408,736, filed as application No. PCT/US2013/046290 on Jun. 18, 2013, now Pat. No. 9,732,067.
(Continued)

(51) Int. Cl.
*A61K 31/4525* (2006.01)
*C07D 405/12* (2006.01)
(Continued)

(52) U.S. Cl.
CPC ........ *C07D 405/12* (2013.01); *A61K 31/4525* (2013.01); *A61K 31/496* (2013.01);
(Continued)

(58) Field of Classification Search
None
See application file for complete search history.

(56) References Cited

U.S. PATENT DOCUMENTS

| 3,336,307 A | 8/1967 | Shen ........................ 260/247.2 |
| 2011/0065686 A1 | 3/2011 | Reyes et al. ............. 514/217.12 |

FOREIGN PATENT DOCUMENTS

| EP | 1321454 A1 | 6/2003 |
| WO | WO 2007/084868 A2 | 7/2007 |
| WO | WO 2008/133734 A2 | 11/2008 |

OTHER PUBLICATIONS

Sausville & Burger. Contributions of human tumor xenografts to anticancer drug development. Cancer Research, 2006, 66: (7). Apr. 1, 2006.*
(Continued)

*Primary Examiner* — Anna Pagonakis
(74) *Attorney, Agent, or Firm* — Licata & Tyrrell P.C.

(57) ABSTRACT

N-substituted sulfonylphenyl-5-nitrofuranyl-2-carboxamide derived compounds, which selectively activate the apop-
(Continued)

totic, but not the adaptive arm, of the Unfolded Protein Response are provides as is their use in the treatment of diseases such as diabetes, Alzheimer's, Parkinson's, hemophilia, lysosomal storage diseases and cancer.

1 Claim, 3 Drawing Sheets

Related U.S. Application Data

(60) Provisional application No. 61/662,099, filed on Jun. 20, 2012.

(51) Int. Cl.
```
C07D 307/71      (2006.01)
A61K 31/496      (2006.01)
A61K 31/5377     (2006.01)
A61K 45/06       (2006.01)
C07C 303/36      (2006.01)
```
(52) U.S. Cl.
CPC .......... *A61K 31/5377* (2013.01); *A61K 45/06* (2013.01); *C07C 303/36* (2013.01); *C07D 307/71* (2013.01)

(56) References Cited

OTHER PUBLICATIONS

Johnson et al. Relationships between drug activity in NCI preclinical in vitro and in vivo models and early clinical trials. British Journal of Cancer, 2001, 84(10), 1424-1431.*
Ameri et al. "Anoxic Induction of ATF-4 through HIF-1-independent Pathways of Protein Stabilization in Human Cancer Cells" Blood 2004 103(5):1876-1882.
Bi et al. "ER Stress-Regulated Translation Increases Tolerance to Extreme Hypoxia and Promotes Tumor Growth" The EMBO Journal 2005 24:3470-3481.
Blais, J. and Bell, J. C. "Novel Therapeutic Targets: The PERKs of Inhibiting the Integrated Stress Response" Cell Cycle 2006 5(24):2874-2877.
Brewer, J. W. and Diehl, J. A. "PERK Mediates Cell-Cycle Exit during the Mammalian Unfolded Protein Response" PNAS 2000 97(23):12625-12630.
Brown, J. M. and Wilson, W. R. "Exploiting Tumour Hypoxia in Cancer Treatment" Nature Reviews Cancer 2004 4:437-447.
Cullinan, S. B. and Diehl, J. A. "PERK-dependent Activation of Nrf2 Contributes to Redox Homeostasis and Cell Survival Following Endoplasmic Reticulum Stress" The Journal of Biological Chemistry 2004 279(19):20108-20117.
Davies et al. "Expression and Splicing of the Unfolded Protein Response Gene XBP-1 Are Significantly Associated with Clinical Outcome of Endocrine-treated Breast Cancer" International Journal of Cancer 2008 123:85-88.
Delépine et al. "EIF2AK3, Encoding Translation Initiation Factor 2-α Kinase 3, Is mutated in Patients with Wolcott-Rallison Syndrome" Nature Genetics 2000 25:406-409.
Feldman et al. "The Unfolded Protein Response: A Novel Component of the Hypoxic Stress Response in Tumors" Molecular Cancer Research 2005 3(11):597-605.
Gupta et al. "PERK Regulates the Proliferation and Development of Insulin-Secreting Beta-Cell Tumors in the Endocrine Pancreas of Mice" PLoS ONE 2009 4(11):e8008.
Hamanaka et al. "PERK and GCN2 Contribute to eIF2α Phosphorylation and Cell Cycle Arrest after Activation of the Unfolded Protein Response Pathway" Molecular Biology of the Cell 2005 16:5493-5501.
Hamanaka et al. "PERK-dependent Regulation of IAP Translation during ER Stress" Oncogene 2009 28(6):910-920.

Harding et al. "Diabetes Mellitus and Exocrine Pancreatic Dysfunction in PERK -/- Mice Reveals a Role for Translational Control in Secretory Cell Survival" Molecular Cell 2001 7:1153-1163.
Iida et al. "PERK eIF2 Alpha Kinase Is Required to Regulate the Viability of the Exocrine Pancreas in Mice" BMC Cell Biology 2007 8:38.
Jorgensen et al. "Cigarette Smoke Induces Endoplasmic Reticulum Stress and the Unfolded Protein Response in Normal and Malignant Human Lung Cells" BMC Cancer 2008 8:229.
Kanekura et al. "ER Stress and Unfolded Protein Response in Amyotrophic Lateral Sclerosis" Molecular Neurobiology 2009 39:81-89.
Koumenis, C. and Wouters, B. G. "'Translating' Tumor Hypoxia: Unfolded Protein Response (UPR)-Dependent and UPR-Independent Pathways" Molecular Cancer Research 2006 4(7):423-436.
Koumenis et al. "Regulation of Protein Synthesis by Hypoxia via Activation of the Endoplasmic Reticulum Kinase PERK and Phosphorylation of the Translation Initiation Factor eIF2α" Molecular and Cellular Biology 2002 22(21):7405-7416.
Larsson et al. "Eukaryotic Translation Initiation Factor 4E-Induced Progression of Primary Human Mammary Epithelial Cells Along the Cancer Pathway Is Associated with Targeted Translational Deregulation of Oncogenic Drivers and Inhibitors" Cancer Research 2007 67(14):6814-6824.
Li et al. "Microwave-Assisted Synthesis of Amides from Various Amines and Benzoyl Chloride Under Solvent-Free Conditions: A Rapid and Efficient Method for Selective Protection of Diverse Amines" Russian Journal of Organic Chemistry 2008 44(3):358-361.
Ma, Y. and Hendershot, L. M. "The Role of the Unfolded Protein Response in Tumour Development: Friend or Foe?" Nature 2004 4:966-977.
Ma et al. "Characterization of Phosphopeptides from Protein Digests Using Matrix-Assisted Laser Desorption/Ionization Time-of-Flight Mass Spectrometry and Nanoelectrospray Quadrupole Time-of-Flight Mass Spectrometry" Rapid Communications in Mass Spectrometry 2001 15:1693-1700.
Ma et al. "Dimerization and Release of Molecular Chaperone Inhibition Facilitate Activation of Eukaryotic Initiation Factor-2 Kinase in Response to Endoplasmic Reticulum Stress" Journal of Biological Chemistry 2002 277:18728-18735.
Marciniak et al. "Activation-Dependent Substrate Recruitment by the Eukaryotic Translation Initiation Factor 2 Kinase Perk" The Journal of Cell Biology 2006 172(2):201-209.
McAlpine et al. "Diabetes, Hyperglycemia, and Accelerated Atherosclerosis: Evidence Supporting a Role for Endoplasmic Reticulum (ER) Stress Signaling" Cardiovascular & Haematological Disorders-Drug Targets 2010 10:151-157.
Nassif et al. "Amyotrophic Lateral sclerosis Pathogenesis: A Journey through the Secretory Pathway" Antioxidants & Redox Signaling 2010 13(12):1955-1989.
Nathan et al. "Detection of the Proto-Oncogene eIF4E in Surgical Margins May Predict Recurrence in Head and Neck Cancer" Oncogene 1997 15:579-584.
O'Connor et al. "Phosphorylation of the Translation Initiation Factor eIF2α Increases BACE1 Levels and Promotes Amyloidogenesis" Neuron 2008 60(6):988-1009.
Paschen, W. "Endoplasmic Reticulum Dysfunction in Brain Pathology: Critical Role of Protein Synthesis" Current Neurovascular Research 2004 1:173-181.
Pervin et al. "Increased Susceptibility of Breast Cancer Cells to Stress Mediated Inhibition of Protein Synthesis" Cancer Research 2008 68(12):4862-4874.
PubChem Compound: cl-cob-III-193 (CID 52940455) made available to public on Jun. 15, 2012.
Romero-Ramirez et al. "XBP1 Is Essential for Survival under Hypoxic Conditions and Is Required for Tumor Growth" Cancer Research 2004 64:5943-5947.
Rouschop et al. "The Unfolded Protein Response Protects Human Tumor Cells during Hypoxia through Regulation of the Autophagy Genes MAP1LC3B and ATG5" The Journal of Clinical Investigation 2010 120(1):127-141.

(56) References Cited

OTHER PUBLICATIONS

Salminen et al. "ER Stress in Alzheimer's Disease: A Novel Neuronal Trigger for Inflammation and Alzheimer's Pathology" Journal of Neuroinflammation 2009 6:41.
Shi et al. "Identification and Characterization of Pancreatic Eukaryotic Initiation Factor 2 α-Subunit Kinase, PEK, Involved in Translational Control" Molecular and Cellular Biology 1998 18(12):7499-7509.
Sonenberg, N. and Hinnebusch, A. G. "Regulation of Translation Initiation in Eukaryotes: Mechanisms and Biological Targets" Cell 2009 136(4):731-745.
Sood et al. "Pancreatic Eukaryotic Initiation Factor-2α Kinase (PEK) Homologues in Humans, *Drosophila melanogaster* and *Caenorhabditis elegans* that Mediate Translational Control in Response to Endoplasmic Reticulum Stress" Biochemical Journal 2000 346:281-293.
Sorrells et al. "Pattern of Amplification and Overexpression of the Eukaryotic Initiation Factor 4E Gene in Solid Tumor" Journal of Surgical Research 1999 85:37-42.
Su et al. "Modulation of the Eukaryotic Initiation Factor 2 α-Subunit Kinase PERK by Tyrosine Phosphorylation" Journal of Biological Chemistry 2008 283:469-475.
Zhang et al. "PERK EIF2AK3 Control of Pancreatic β Cell Differentiation and Proliferation Is Required for Postnatal Glucose Homeostasis" Cell Metabolism 2006 491-497.
International Search Report from PCT/US2013/046290, dated Dec. 3, 2013.
Preliminary Report on Patentability from PCT/US2013/046290, dated May 26, 2015.
Office Communication dated Jun. 10, 2015 in U.S. Appl. No. 14/408,736 filed Dec. 17, 2014.
Office Communication dated Nov. 16, 2015 in U.S. Appl. No. 14/408,736 filed Dec. 17, 2014.
Office Communication dated Apr. 13, 2016 in U.S. Appl. No. 14/408,736 filed Dec. 17, 2014.
Office Communication dated Jul. 19, 2016 in U.S. Appl. No. 14/408,736 filed Dec. 17, 2014.
Office Communication dated Aug. 24, 2016 in U.S. Appl. No. 14/408,736 filed Dec. 17, 2014.
Office Communication dated Oct. 20, 2016 in U.S. Appl. No. 14/408,736 filed Dec. 17, 2014.
Office Communication dated Nov. 14, 2016 in U.S. Appl. No. 14/408,736 filed Dec. 17, 2014.
Office Communication dated May 3, 2017 in U.S. Appl. No. 14/408,736 filed Dec. 17, 2014.

* cited by examiner

COMPOUNDS AND METHODS FOR ACTIVATING THE APOPTOTIC ARM OF THE UNFOLDED PROTEIN RESPONSE

INTRODUCTION

This patent application is a divisional of U.S. Ser. No. 14/408,736 filed Dec. 17, 2014, which is the U.S. National Phase of PCT/US2013/046290 filed Jun. 18, 2013, which claims the benefit of priority from U.S. Provisional Application Ser. No. 61/662,099, filed Jun. 20, 2012, the contents of which are incorporated herein by reference in their entireties.

This invention was made with government support under contract number 1 R03 MH089782-01 awarded by the National Institutes of Health. The government has certain rights in the invention.

BACKGROUND OF THE INVENTION

Defective protein processing within the secretory pathway is an integral component of many genetic and environmental diseases. Diverse disease states ranging from diabetes, Alzheimer's disease, and Parkinson's disease, to hemophilia and lysosomal storage diseases have all been characterized by folding defects or impaired transport from the endoplasmic reticulum (ER). It has been shown that deregulation of protein synthesis may be a key component in the pathogenesis of cancer and metastasis (Larsson, et al. (2007) *Cancer Res.* 67:6814-24; Sorrells, et al. (1999) *J. Surg. Res.* 85:37-42; Sonenberg & Hinnebusch (2009) *Cell* 136:731-45; Nathan, et al. (1997) *Oncogene* 15:579-84; Pervin, et al. (2009) *Cancer Res.* 68:4862-74). When misfolded protein accumulates in the ER lumen, the cell activates the Unfolded Protein Response (UPR) to clear the misfolded proteins and restore homeostatic protein processing. When a stress is prolonged or robust, the UPR employs a genetic pathway that results in cell death.

Stress stimuli that activate UPR include hypoxia, disruption of protein glycosylation (glucose deprivation), depletion of luminal ER calcium, or changes in ER redox status (Ma & Hendershot (2004) *Nat. Rev. Cancer* 4:966-77; Feldman, et al. (2005) *Mol. Cancer Res.* 3:597-605). These perturbations result in the accumulation of unfolded or mis-folded proteins in the ER, which is sensed by resident ER membrane proteins. These proteins activate a coordinated cellular response to alleviate the impact of the stress and enhance cell survival. Responses include an increase in the level of chaperone proteins to enhance protein re-folding, degradation of the mis-folded proteins, and translational arrest to decrease the burden of proteins entering the ER. These pathways also regulate cell survival by modulating apoptosis (Ma & Hendershot (2004) supra; Feldman, et al. (2005) supra; Hamanaka, et al. (2009) *Oncogene* 28:910-20) and autophagy (Rouschop, et al. (2010) *J. Clin. Invest.* 120:127-41), and can trigger cell death under conditions of prolonged ER stress.

Three ER membrane proteins have been identified as primary effectors of the UPR: protein kinase R (PKR)-like ER kinase (PERK), inositol-requiring gene 1 α/β (IRE1), and activating transcription factor 6 (ATF6) (Ma & Hendershot (2004) supra). Under normal conditions these proteins are held in the inactive state by binding to the ER chaperone GRP78 (BiP). Accumulation of unfolded proteins in the ER leads to release of GRP78 from these sensors resulting in their activation (Ma, et al. (2002) *J. Biol. Chem.* 277:18728-35). PERK is a type I ER membrane protein containing a stress-sensing domain facing the ER lumen, a transmembrane segment, and a cytosolic kinase domain (Shi, et al. (1998) *Mol. Cell Biol.* 18:7499-509; Sood, et al. (2000) *Biochem. J.* 346(Pt 2):281-93). Release of GRP78 from the stress-sensing domain of PERK results in oligomerization and autophosphorylation at multiple serine, threonine and tyrosine residues (Ma, et al. (2001) *Rapid Commun. Mass Spectrom.* 15:1693-700; Su, et al. (2008) *J. Biol. Chem.* 283:469-75). The major substrate for PERK is the eukaryotic initiation factor 2α (eIF2α) at serine-51 (Marciniak, et al. (2006) *J. Cell Biol.* 172:201-9). This site is also phosphorylated by other PERK family members (general control non-repressed 2 (GCN2), PKR, and heme-regulated kinase) in response to different stimuli, and by pharmacological inducers of ER stress such as thapsigargin and tunicamycin. Phosphorylation of eIF2α converts it to an inhibitor of eIF2B, which hinders the assembly of the 40S ribosome translation initiation complex and consequently reduces the rate of translation initiation. Among other effects, this leads to a loss of cyclin D1 in cells resulting in arrest in the G1 phase of the cell division cycle (Brewer & Diehl (2000) *Proc. Natl. Acad. Sci. USA* 97:12625-30; Hamanaka, et al. (2005) *Mol. Biol. Cell* 16:5493-501). Furthermore, translation of certain messages encoding downstream effectors of eIF2α, ATF4 and CHOP (C/EBP homologous protein; GADD153), which modulate cellular survival pathways, is increased upon ER stress.

A second PERK substrate, Nrf2, regulates cellular redox potential, contributes to cell adaptation to ER stress, and promotes survival (Cullinan & Diehl (2004) *J. Biol. Chem.* 279:20108-17). The normal function of PERK is to protect secretory cells from ER stress. Phenotypes of PERK knockout mice include diabetes, due to loss of pancreatic islet cells, skeletal abnormalities, and growth retardation (Harding, et al. (2001) *Mol. Cell* 7:1153-63; Zhang, et al. (2006) *Cell. Metab.* 4:491-7; Iida, et al. (2007) *BMC Cell Biol.* 8:38). These features are similar to those seen in patients with Wolcott-Rallison syndrome, who carry germline mutations in the PERK gene (Delepine, et al. (2000) *Nat. Genet.* 25:406-9). IRE1 is a transmembrane protein with kinase and endonuclease (RNAse) functions (Feldman, et al. (2005) supra; Koumenis & Wouters (2006) *Mol. Cancer Res.* 4:423-36). Under ER stress, it undergoes oligomerization and autophosphorylation, which activates the endonuclease to excise an intron from unspliced X-box binding protein 1 (XBP1) mRNA. This leads to the synthesis of truncated XBP1, which activates transcription of UPR genes.

The third effector of UPR, ATF6, is transported to the golgi upon ER stress, where it is cleaved by proteases to release the cytosolic transcription domain. This domain translocates to the nucleus and activates transcription of UPR genes (Feldman, et al. (2005) supra; Koumenis & Wouters (2006) supra).

Tumor cells experience episodes of hypoxia and nutrient deprivation during their growth due to inadequate blood supply and aberrant blood vessel function (Brown & Wilson (2004) *Nat. Rev. Cancer* 4:437-47; Blais & Bell (2006) *Cell Cycle* 5:2874-7). Thus, they are likely to be dependent on active UPR signaling to facilitate their growth. Consistent with this, mouse fibroblasts derived from PERK$^{-/-}$, XBP1$^{-/-}$, and ATF4$^{-/-}$ mice, and fibroblasts expressing mutant eIF2α show reduced clonogenic growth and increased apoptosis under hypoxic conditions in vitro and grow at substantially reduced rates when implanted as tumors in nude mice (Koumenis, et al. (2002) *Mol. Cell Biol.* 22:7405-16; Romero-Ramirez, et al. (2004) *Cancer Res.* 64:5943-7; Bi, et al. (2005) *EMBO J.* 24:3470-81). Human tumor cell lines carrying a dominant-negative PERK that lacks kinase activity also showed increased apoptosis in vitro under hypoxia and impaired tumor growth in vivo (Bi, et al. (2005) supra). In these studies, activation of the UPR was observed in regions within the tumor that coincided with hypoxic areas. These areas exhibited higher rates of apoptosis compared to tumors with intact UPR signaling. Further evidence supporting the role of PERK in promoting tumor growth is the observation that the number, size, and vascularity of insulinomas arising in transgenic mice expressing the SV40-T antigen in the insulin-secreting beta cells, was profoundly reduced in PERK$^{-/-}$ mice compared to wild-type control (Gupta, et al. (2009) *PLoS One* 4:e8008).

Activation of the UPR has also been observed in clinical specimens. Human tumors, including those derived from cervical carcinomas and glioblastomas (Bi, et al. (2005) supra), as well as lung cancers (Jorgensen, et al. (2008) *BMC Cancer* 8:229) and breast cancers (Ameri, et al. (2004) *Blood* 103:1876-82; Davies, et al. (2008) *Int. J. Cancer* 123:85-8) show elevated levels of proteins involved in UPR compared to normal tissues.

Loss of endoplasmic reticulum homeostasis and accumulation of misfolded proteins can contribute to a number of disease states including cardiovascular and degenerative diseases (Paschen (2004) *Curr. Neurovas. Res.* 1(2):173-181) such as Alzheimer's disease (Salminen, et al. (2009) *J. Neuroinflamm.* 6:41; O'Connor, et al. (2008) *Neuron* 60(6): 988-1009), Parkinson disease, Huntington's disease, amyotrophic lateral sclerosis (Kanekura, et al. (2009) *ALS Mol. Neurobiol.* 39(2):81-89; Nassif, et al. (2010) *Antioxid. Redox Signal.* 13(12):1955-1989), myocardial infarction, cardiovascular disease, atherosclerosis (McAlpine, et al. (2010) *Cardio. Hematolog. Dis. Drug Targets* 10(2):151-157), and arrhythmias.

In a prior screen of ~66,000 compounds, two thiuram compounds, disulfiram and NSC-1771, were identified as non-selective hits that could potently induce both the CHOP (apoptotic) and XBP1 (adaptive) arms of the UPR.

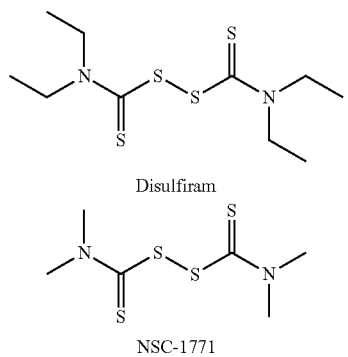

NSC-1771 is used commercially as a fungicide and is known to cause dyschondoplasia in the offspring of chickens who consume the grain from crops treated with this compound. Therefore, NSC-1771 was not followed-up beyond hit validation. Disulfiram (bis(diethylthiocarbamoyl) disulfide) is marketed commercially as ANTABUSE and is indicated for aversion therapy to treat chronic alcoholism.

However, because these compounds are not selective, there remains a need in the art for selective activators of the PERK/eIF2α/CHOP (apoptotic), but not the IRE1/XBP1 (adaptive) UPR subpathways.

SUMMARY OF THE INVENTION

This invention features N-substituted sulfonylphenyl-5-nitrofuranyl-2-carboxamide-derived compounds and methods for using the same to selectively activate the apoptotic arm of the Unfolded Protein Response. An activator of the invention has the structure of Formula I, or a pharmaceutically acceptable salt, ester or prodrug thereof, Formula I

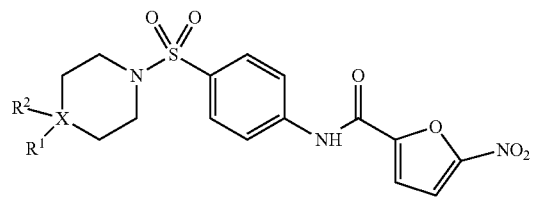

wherein
X is C, N or O; and
$R^1$ and $R^2$ are each independently a hydrogen, hydroxyl, halo, or a substituted or unsubstituted alkyl or alkoxy group; or
$R^1$ and $R^2$ together form a substituted or unsubstituted cycloalkyl group,
with the proviso that when X is O, $R^1$ and $R^2$ are absent.

A pharmaceutical composition containing a compound of Formula I is also provided, as is a method for synthesizing a compound of Formula I by (a) treating a 4-substituted piperidine with an aryl sulfonyl chloride to produce a sulfonamide; (b) contacting the sulfonamide with a reducing agent to produce an aniline; and (c) treating the aniline with 5-nitrofuran acyl chloride under microwave irradiation.

This invention also provides methods for selectively activating the apoptotic, but not the adaptive arm, of the UPR, and treating or lessening the severity of a UPR-related disease in a subject by providing a compound of Formula I. In some embodiments, the UPR-related disease is a precancerous syndrome, Alzheimer's disease, stroke, Type 1 diabetes, Parkinson disease, Huntington's disease, amyotrophic lateral sclerosis, myocardial infarction, cardiovascular disease, atherosclerosis, arrhythmias, age-related macular degeneration or a lysosomal storage disorder. In other embodiments, the UPR-related disease is cancer. In still other embodiments, the method includes the co-administration of at least one anti-neoplastic agent.

BRIEF DESCRIPTION OF THE DRAWINGS

FIG. 3A, Six OSCC cell lines exposed to ML291 for 24 hours. FIG. 3B, Four ovarian cancer cell lines exposed to ML291 for 24 hours.

DETAILED DESCRIPTION OF THE INVENTION

Figure 1:
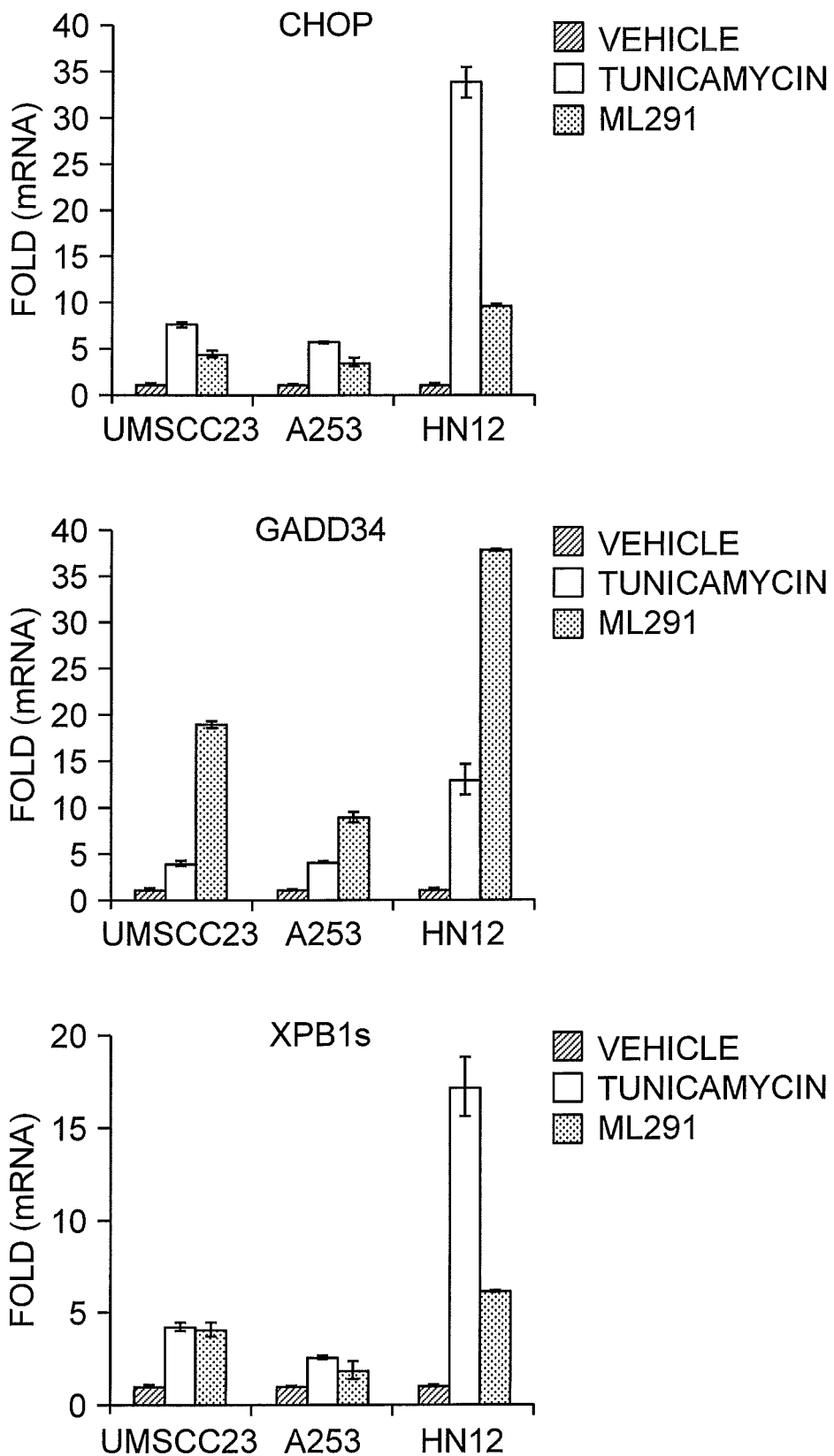
FIG. 1 shows that ML291 induces UPR in a panel of oral squamous cell carcinoma cells. Shown are the results of qRT-PCR analysis of CHOP, GADD34 and XBP1s after 4 hours of ML291 treatment (5 μM).

This invention pertains to N-substituted sulfonylphenyl-5-nitrofuranyl-2-carboxamide-derived compounds and their use in selectively activating the apoptotic, but not the adaptive arm, of the UPR. The compounds of this invention are first-in-class, potent (ML291: 762 nM $EC_{50}$), not generally cytotoxic, activate genes associated with the apoptotic arm of the UPR (by qRT-PCR), and demonstrate efficacy in inducing cell death through activation of the apoptotic arm in relevant cells. The hit compound for the series was identified through a high-throughput screen of the NIH Molecular Libraries Small Molecule Repository (MLSMR) of >350,000 compounds through complementary cell-based reporter assays using stably transfected CHO-K1 cells that specifically identify activators of the PERK/eIF2α/CHOP (apoptotic), but not the IRE1/XBP1 (adaptive) UPR sub-pathways. Medicinal chemistry was carried out to optimize the hit and provide analogs thereof. The hit compound and its analogs find use in characterizing the molecular mechanism of UPR activation through PERK and ATF6, the removal of aberrant or pathological "stressed" cells, and in the treatment of diseases and conditions such as such as diabetes, Alzheimer's, Parkinson's, hemophilia, cancer (e.g., breast, lung, or head and neck squamous cell carcinoma) and lysosomal storage diseases.

Accordingly, this invention is an N-substituted sulfonylphenyl-5-nitrofuranyl-2-carboxamide-derived compound of Formula I, or an analog, stereoisomer, tautomer, pharmaceutically acceptable salt, or prodrug thereof. Compounds of Formula I have the structure:

Formula I

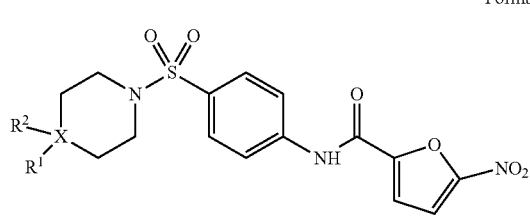

wherein

X is C, N or O; and $R^1$ and $R^2$ are each independently a hydrogen, hydroxyl, halo, or a substituted or unsubstituted alkyl or alkoxy group; or $R^1$ and $R^2$ together form a substituted or unsubstituted cycloalkyl group, with the proviso that when X is O, $R^1$ and $R^2$ are absent.

As is conventional in the art, a hydroxyl group is —OH; and a halo group is fluorine, chlorine, bromine or iodine.

As used herein, the term "alkyl" employed alone or in combination with another term includes a straight or branched chain hydrocarbon. If not otherwise defined, alkyl has 1 to 6 carbon atoms. Examples of "$C_{1-6}$ alkyl" are alkyl residues containing 1, 2, 3, 4, 5, or 6 carbon atoms are methyl, ethyl, propyl, butyl, pentyl, or hexyl, the n-isomers of all these residues, isopropyl, isobutyl, 1-methylbutyl, isopentyl, neopentyl, isohexyl, sec-butyl, tert-butyl or tert-pentyl.

The term "alkyoxy" includes an alkyl, as defined herein, bonded to oxygen. Methyoxy, ethyoxy, n-propyloxy, isopropyloxy, n-butyloxy, isobutyloxy, sec-butyloxy, tert-butyloxy, n-pentyloxy, isopentyloxy, neo-pentyloxy, n-hexyloxy, isohexyloxy, and the like are exemplified as "alkyoxy."

A "cycloalkyl" group refers to a saturated closed ring structure with 5-7 carbon atoms in the ring. Examples of the cycloalkyl groups are cyclopentyl, cyclohexyl, and cycloheptyl.

If not otherwise defined, alkyl, alkoxy, and cycloalkyl may be unsubstituted or mono, di- or tri-substituted independently of one another by groups such as, for example, —F, —Cl, —Br, —I, —$CF_3$, —$NO_2$, —CN, —$NH_2$, —COOH, —OH, —$OCH_3$, —$OCF_3$, —$CONH_2$, -alkyl, or -alkoxy group.

In some embodiments of the invention, X is C, $R^1$ is hydrogen and $R^2$ is a halo group. In other embodiments, X is C, $R^1$ is hydrogen and $R^2$ is a fluoro group. In still other embodiments, X is C, $R^1$ is hydrogen and $R^2$ is a substituted alkyl group. In specific embodiments, the compound of the invention is Analog 3 or Analog 4.

Analog 3

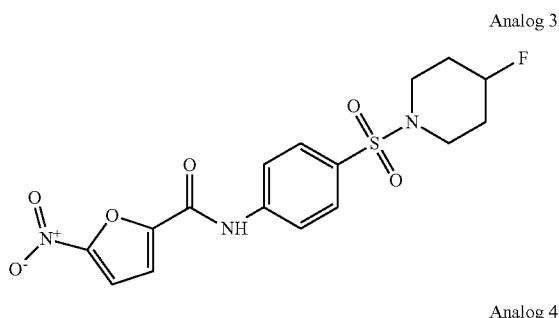

Analog 4

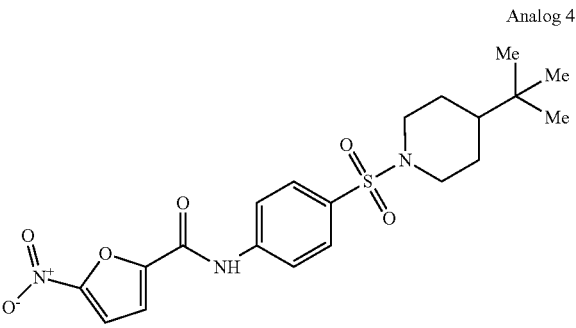

Exemplary compounds of Formula I are presented in Examples 10 and 11. The compounds disclosed herein can be used as lead compounds to identify additional, structurally related compounds, analogs or derivatives which activate CHOP. For example, the compounds disclosed herein can be modified based upon additional SAR analysis to include additional substituents (e.g., O, N, S, OH, $CH_3$, halo groups, phenyl groups, alkyl groups, etc.), remove substituents (e.g., O, N, S, OH, $CH_3$, halo groups, phenyl groups, alkyl groups, etc.), or substitute groups (e.g., substitute one halo group for another) in order to provide analogs with improved activity, solubility, and/or efficacy. As with the initial screens, modified compounds or compound analogs or derivatives can be screened via in vitro methods to determine activity.

The compounds of the invention can be prepared by the method presented in Scheme 1, wherein a 4-substituted piperidine of Formula II (wherein X is C and $R^1$ and $R^2$ are as defined above) is treated with an aryl sulfonyl chloride to produce a sulfonamide and the sulfonamide is subsequently contacted with a reducing agent to produce an aniline of Formula III. A compound of Formula I is then prepared by treating the aniline of Formula III with 5-nitrofuran acyl chloride under microwave irradiation.

SCHEME 1

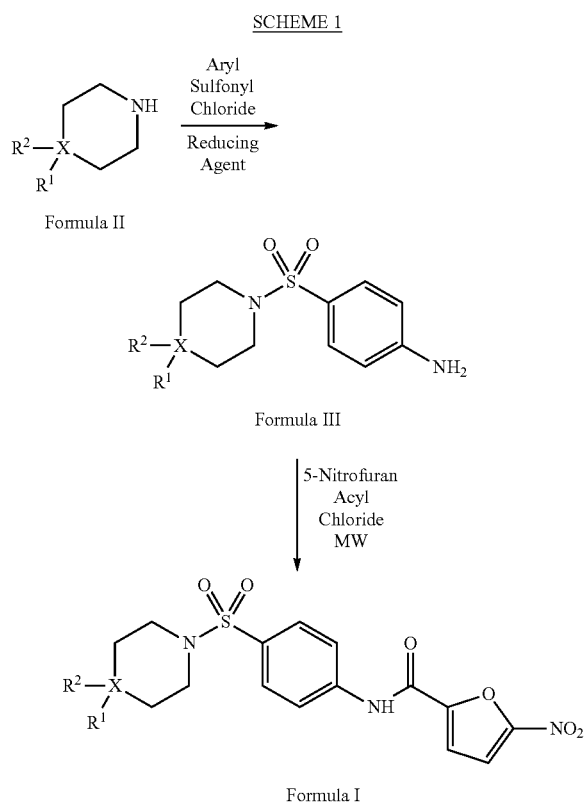

Compounds of the invention can be used as is or prepared as pharmaceutically acceptable salts. As used herein, the term "pharmaceutically acceptable salt" refers to those salts of the compounds of Formula I which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. See, e.g., Berge, et al. (1977) *J. Pharmaceutical Sciences* 66:1-19. Salts can be prepared in situ during the final isolation and purification of the compounds of the invention, or separately by reacting a free base with a suitable organic acid. Examples of pharmaceutically acceptable salts include, but are not limited to, nontoxic acid addition salts formed from amino group and an inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "pharmaceutically acceptable prodrug" as used herein refers to those prodrugs of the compounds of Formula I which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug," as used herein refers to a compound which is convertible in vivo by metabolic means (e.g., by hydrolysis) to afford any compound delineated by the formula of the instant invention. Various forms of prodrugs are known in the art, for example, as discussed in Bundgaard (ed.) *Design of Prodrugs*, Elsevier (1985); Widder, et al. (ed.) *Methods in Enzymology*, vol. 4, Academic Press (1985); Krogsgaard-Larsen, et al. (ed.) *Design and Application of Prodrugs, Textbook of Drug Design and Development*, Chapter 5, 113-191 (1991); Bundgaard, et al. (1992) *J. Drug Deliv. Rev.* 8:1-38; Bundgaard (1988) *J. Pharmaceut. Sci.* 77:285; Higuchi & Stella (eds.) *Prodrugs as Novel Drug Delivery Systems*, American Chemical Society (1975).

To demonstrate activity, candidate compounds, analogs, stereoisomers, tautomers, pharmaceutically acceptable salts, or prodrugs thereof, can be tested as described in the Examples herein for their ability to activate the apoptotic arm of the UPR. The activity of the compounds can be assayed utilizing methods known in the art and/or those methods presented herein. For example, quantitative real-time reverse-transcription PCR (qRT-PCR) analysis or northern blot analysis can be carried out to determine whether CHOP transcripts, e.g., GADD34 and proapoptotic BH3-only protein BIM, are induced in the presence of a candidate compound, analog, stereoisomer, tautomer, pharmaceutically acceptable salt, or prodrug thereof. Compounds demonstrating the ability to selectively activate CHOP can be tested in known cell or animal models of cancer, Alzheimer's disease, diabetes or a lysosomal storage disease.

For therapeutic and prophylactic applications, one or more compounds of the invention can be formulated as a pharmaceutical composition. A pharmaceutical composition contains a therapeutically effective amount of a compound of this invention formulated together with one or more pharmaceutically acceptable carriers. As used herein, the term "pharmaceutically acceptable carrier" means a nontoxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide;

alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, intratumorally, intracerebrally, intracerebroventricularly, or intrathecally and includes an oral or nasal spray. In particular embodiments, the pharmaceutical composition is a formulation suitable for intratumoral, intracerebral, intracerebroventricular, or intrathecal administration. Such formulations include injectable formulations, implantable reservoirs, infusions or oral or nasal sprays.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

According to the methods of treatment of this invention, a subject, such as a human or lower mammal, is administered an effective amount of a compound of the invention, in such amounts and for such time as is necessary to achieve the desired result. The term "effective amount" of a compound of the invention, as used herein, means a sufficient amount of the compound so as to decrease the signs or symptoms of the disease or disorder in a subject. The actual amount effective for a particular application will depend, inter alia, on the condition being treated. For example, when administered in methods to treat Alzheimer's disease, such compositions will contain an amount of active ingredient effective to achieve the desired result (e.g., activating CHOP, protecting against aberrant mitochondrial and neuronal function, improving learning memory, and/or reducing mitochondrial and cerebral Aβ accumulation). Similarly, when administered in methods to treat cancer, e.g., breast, hematopoietic, lung, laryngeal, pharyngeal and head and neck squamous cell carcinoma, such compositions will contain an amount of active ingredient effective to achieve the desired result of activating CHOP and/or reducing tumor size, growth or formation. Determination of a therapeutically effective amount of a compound of the invention is well within the capabilities of those skilled in the art.

It will be understood that the total daily usage of the compounds and compositions of this invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to this invention include administration to a subject in need of such treatment from about 10 mg to about 1000 mg of the compound(s) of this invention per day in single or multiple doses.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

As is well known in the art, therapeutically effective amounts for use in humans can also be determined from animal models. For example, a dose for humans can be formulated to achieve a concentration that has been found to be effective in animals. The dosage in humans can be adjusted by monitoring activation of CHOP and adjusting the dosage upwards or downwards. Adjusting the dose to achieve maximal efficacy in humans based on animal models and other methods as are well-known in the art is well within the capabilities of the ordinarily skilled artisan.

Having demonstrated that the compounds of this invention can activate the apoptotic arm of UPR, this invention also includes a method for selectively activating the apoptotic, but not the adaptive arm, of the UPR. The method involves contacting a cell with an effective amount of a compound disclosed herein so that the apoptotic arm, but not the adaptive arm, of the UPR is activated. Activation of the apoptotic arm can be monitored by determining whether there is a measurable change in the expression of one or more genes associated with the apoptotic arm of the UPR (e.g., BIM, GADD34, endoplasmic oxidoreductin 1-alpha (ERO1α), and Tribbles-related protein 3 (TRB3)) or whether there is a measurable increase in cell death. In certain embodiments, the cell is a cancer cell.

In particular embodiments of this invention, a pharmaceutical composition containing a CHOP activator, pharmaceutically acceptable salt, ester or prodrug thereof, is useful in the treatment of conditions wherein the underlying pathology is attributable to (but not limited to) modulation of the UPR pathway, for example, cancer and more specifically cancers of the head and neck, breast, colon, lung, pancreas and skin. Not wishing to be bound by theory, it is believed that CHOP-specific activators will overwhelm the adaptive UPR capacity of malignant cells, while healthy cells, with low or no basal UPR activation, would be able to mount an effective UPR and overcome the chemotherapeutic challenge and directly induce apoptosis. Accordingly, another aspect of the invention is directed to methods of treating such UPR-related diseases or conditions.

In some embodiments, the invention relates to a method for treating or lessening the severity of cancers selected from the group of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, lung (e.g., small cell lung cancer, non-small cell lung cancer, squamous cell carcinoma, adenocarcinoma, and large cell carcinoma), head and neck, kidney, liver, melanoma, ovarian, pancreatic (e.g., insulinomas, adenocarcinoma, ductal adenocarcinoma, adenosquamous carcinoma, acinar cell carcinoma, and glucagonoma), adenocarcinoma, ductal adenocarcinoma, adenosquamous carcinoma, acinar cell carcinoma, glucagonoma, insulinoma, colon, prostate, breast (e.g., inflammatory breast cancer, ductal carcinoma, and lobular carcinoma), sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In other embodiments, the invention relates to a method for treating or lessening the severity of pre-cancerous syndromes in a mammal, including a human, wherein the pre-cancerous syndrome is cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

In still other embodiments, the invention relates to a method for treating or lessening the severity of additional UPR-related diseases including Type 1 diabetes, Alzheimer's disease, stroke, Parkinson disease, Huntington's disease, amyotrophic lateral sclerosis, myocardial infarction, cardiovascular disease, atherosclerosis, arrhythmias, hemophilia, age-related macular degeneration, and lysosomal storage disorder.

The methods of treatment of the invention involve administering an effective amount of a compound according to Formula I or a pharmaceutically acceptable salt, ester or prodrug thereof to a subject in need thereof. As used herein, "subject" refers to a human or other animal. Suitably the subject is a human. By the term "treating" and derivatives thereof as used herein, is meant prophylactic and therapeutic therapy. Prophylactic therapy is appropriate, for example, when a subject is considered at high risk for developing cancer, or when a subject has been exposed to a carcinogen.

The compounds of Formula I or pharmaceutically acceptable salts, esters or prodrugs thereof may be administered by any suitable route of administration, including systemic administration. Systemic administration includes oral administration, and parenteral administration. Parenteral administration refers to routes of administration other than enteral, transdermal, or by inhalation, and is typically by injection or infusion. Parenteral administration includes intravenous, intramuscular, intraperitoneal injection, and subcutaneous injection or infusion.

Additionally, the compounds of Formula I or pharmaceutically acceptable salts, esters or prodrugs thereof may be co-administered with at least one other active agent known to be useful in the treatment of cancer. By the term "co-administration," as used herein, is meant either simultaneous administration or any manner of separate sequential administration of a CHOP activating compound, as described herein, and a further active agent or agents, known to be useful in the treatment of cancer, including chemotherapy and radiation treatment. The term active agent or agents, as used herein, includes any compound or therapeutic agent known to or that demonstrates advantageous properties when administered to a subject in need of treatment for cancer. Preferably, if the administration is not simultaneous, the compounds are administered in a close time proximity to each other. Furthermore, it does not matter if the compounds are administered in the same dosage form, e.g., one compound may be administered by injection and another compound may be administered orally.

Typically, any anti-neoplastic agent that has activity against a susceptible tumor may be co-administered in the treatment of cancer in this invention. Examples of such agents can be found in *Cancer Principles and Practice of Oncology* by Devita & Hellman (Ed.), 6$^{th}$ Edition (2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; anti-metabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

The invention is described in greater detail by the following non-limiting examples.

EXAMPLE 1

Materials and Methods

Protocol for UPR-CHOP Primary Assay. The purpose of this assay was to detect activators of the PERK-eIF2α-CHOP (apoptotic) arm of the Unfolded Protein Response pathway.

Materials. DPBS and Heat-inactivated Fetal Bovine Serum were from Hyclone; F12 nutrient mix HAMs medium, Penicillin/Streptomycin, liquid, L-glutamine (100×), MEM Non-Essential Amino Acids Solution 10 mM (100×), and Trypsin-EDTA 0.25% were from Invitrogen; T225 TC Flasks were from Nunc; 40 µm cell strainers were from BD; 1536-well white solid bottom TC plates were from Aurora Biotechnology; Tunicamycin was from Sigma-Aldrich; and STEADY-GLO Luciferase Assay System was from Promega.

Procedure for Expanding and Maintaining Cells. CHO-CHOP cells were seeded into T225 flasks at $3.75 \times 10^5$ cells. Cells were passaged twice a week. Confluency was maintained at <75%. After 3 days incubation in 5% $CO_2$, ~2.5× $10^7$ cells were typically observed per T225 flask. Once the cells had reached confluency, old medium was aspirated and the flasks were washed with 20 mL DPBS per T225 flask. Cells were left in DPBS for about 30 seconds. Subsequently, 6.5 mL 0.05% trypsin solution was added into the flask and the flask was rocked gently so that the solution covered the surface. The cells were allowed to detach by incubating at room temperature for about 4 minutes. The flask was washed with 25 mL fresh growth media and the cell suspension was collected in a 50 mL sterile conical tube. The collected cells were centrifuged at 900 rpm for 5 minutes and re-suspended in 1 mL fresh growth media. An additional 19 mL of growth media was added and the tube was mixed gently. The cell suspension was filtered with a cell strainer and the cells were counted. Stock flasks were prepared with $3.00 \times 10^5$ cells per T225 flask for 4 days incubation or $3.75 \times 10^5$ cells per T225 flask for 3 days incubation.

Procedure for Preparing Cells for the Screening Assay. As above, cells were grown to confluency, washed, and detached with 5 mL trypsin solution for 4 minutes at room temperature. The flask was washed with 25 mL fresh growth media and the cell suspension was collected in a 50 mL sterile conical tube. The cells were centrifuged at 500 rpm for 10 minutes and re-suspended carefully in 1 mL fresh assay medium. An additional 19 mL of assay media was added the cells were mixed gently. The cell suspension was filtered with a cell strainer and the number of cells was counted. Cell density was adjusted to $1.0 \times 10^5$ cells/mL in medium.

Plate Map. Positive control (P) in columns 1 and 2, 10 μg/mL Tunicamycin; Negative control (N) in columns 3 and 4, No Tunicamycin; and Test compound (T) in columns 5-48, No Tunicamycin.

Assay Procedure. On day 1, cell suspensions were prepared and 500 cells in 5 μL of assay media were plated in the wells of columns 1-48 of a 1536-well assay plate. The plates were centrifuged at 500 rpm for 1 minute and subsequently incubated at 37° C., 100% relative humidity, 5% $CO_2$ for 16-18 hours.

On day 2, 25 nL of test compounds (2 mM stock concentration) were transferred into the wells of the assay plate so that the final concentration of the test compounds was 10 μM (0.5% DMSO). The reporter cells can tolerate up to ~4% before UPR activation or toxicity is observed. The plates were centrifuged at 1000 rpm for 1 minute and subsequently incubated at 37° C., 100% relative humidity, 5% $CO_2$ for 6 hours.

Following the 6-hour incubation the plate was incubated for 10 minutes at room temperature and 3 μL of STEADY-GLO was added to each well. The plates were centrifuged at 2000 rpm for 2 minutes and subsequently incubated at room temperature for 10 minutes. Luminescence was measured with a luminometer.

EXAMPLE 2

Library Screen for PERK/eIF2α/CHOP Activators

A high-throughput screen of the NIH Molecular Libraries Small Molecule Repository (MLSMR) of >350,000 compounds was carried out using complementary cell-based reporter assays using stably transfected CHO-K1 cells that specifically identify activators of the PERK/eIF2α/CHOP (apoptotic), or the IRE1/XBP1 (adaptive) UPR sub-pathways.

The MLPCN library of approximately 330,000 compounds was tested in the UPR-CHOP primary screen utilizing a luciferase-based reporter expressed in a CHO cell line to identify activators of the CHOP apoptotic pathway. During the performance of the screening campaign, 1125 compounds with activity ≥40% at a single concentration of 10 μM were identified. Liquid samples for 1125 compounds were obtained.

The liquid samples were first confirmed at a single-point concentration of 10 μM in the NTR1 HCS primary assay. Of the liquid samples, 674 compounds were confirmed to have at least 32% activity at a 10 μM assay concentration. The confirmed compounds were further tested in dose response in the UPR-CHOP primary assay to obtain $EC_{50}$ values. In addition, confirmed compounds were also dosed out in the CHO-XBP1-luciferase reporter cell line to identify compounds that were selective for the CHOP apoptotic over the adaptive XBP1 pathway.

Chemistry and cheminformatics resources were then employed in the selection of both novel and chemically tractable molecules to pursue for a UPR-CHOP selective probe. Structures of interest and analogs thereof were obtained. In addition, medicinal chemistry efforts were initiated on a small group of promising scaffolds.

EXAMPLE 3

Structure-Activity Relationship (SAR) Analysis

The high throughput screening effort and subsequent validation produced two chemotypes, which were further explored by SAR analysis for potency, selectivity, the absence of reactive functionality, synthetic accessibility, physiochemical properties, and hit rate in unrelated PUBCHEM assays. SAR testing of re-constituted powders encompassed dose response testing of compounds in two assays: UPR-CHOP and UPR-XBP1 assays. The sulfonamidebenzamide series and the benzothiazole series, represented by SID 104222717 and SID 104222735, respectively, were found to have low micromolar potency for CHOP while not exhibiting activity on XBP1 (>70-80 μM).

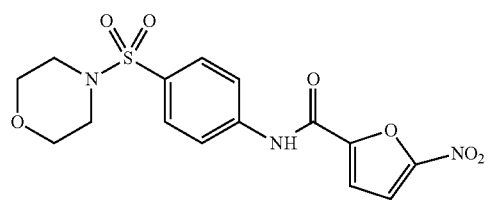

Sulfonamidebenzamides
SID 104222717
CID 2309197
CHO $EC_{50}$ = 2.02 μM
XBP1 $EC_{50}$ > 71 μM

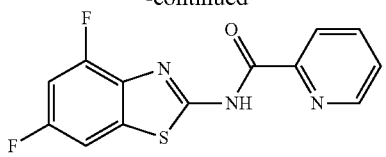

Benzothiazoles
SID 104222735
CID 49852459
CHO EC$_{50}$ = 4.92 µM
XBP1 EC$_{50}$ > 80 µM Both chemotypes were developed in parallel, and the UPR CHOP and XPB1 assay data were used to drive the SAR effort. Once promising compounds were identified that met or were close to meeting the probe criteria (CHOP EC$_{50}$<1 µM, selectivity over XBP1>10-fold), then compounds were assessed in more elaborate secondary assays.

For the benzothiazole series, it was clear from the synthesized SAR set that the 2-pyridyl moiety was necessary to retain CHOP activity, as 3- or 4-pyridyl derivatives lost activity (CHOP EC$_{50}$>80 µM). Substitution of the phenyl ring of the benzothiazole with electron withdrawing group(s) was also necessary for CHOP activity (e.g., dimethyl substitution afforded an analog devoid of CHOP activity). However, the collection of ~20 analogs revealed a flat SAR with many analogs possessing CHOP EC$_{50}$ values in the 4.7-9.9 µM range. As a result, the chemotype was deprioritized in favor of more promising results being observed with the other scaffold of interest.

For the sulfonamidebenzamide series, modifications first focused on the N-morpholine group of the parent scaffold (Table 1).

TABLE 1

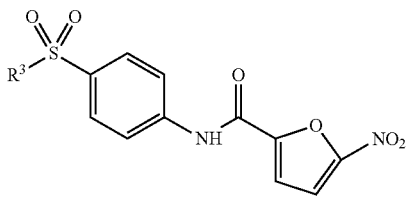

| Entry | R$^3$ | UPR CHOP Assay Potency$^a$ EC$_{50}$ (µM) | UPR XBP1 Assay Potency$^b$ EC$_{50}$ (µM) | Selectivity (XBP1/CHOP) x-fold |
|---|---|---|---|---|
| 1 | N-morpholine | 2.28$^3$ | >80$^4$ | >35.1 |
| 2 | 3,5-dimethyl-N-morpholine | 1.36$^3$ | >80$^3$ | >58.8 |
| 3 | N-piperazine | 26.43$^3$ | >80$^3$ | >3.0 |
| 4 | 4-pyran | 1.19$^3$ | >80$^2$ | >67.2 |
| 5 | cyclohexyl | 0.68$^3$ | >80$^3$ | >117.6 |
| 6 | phenyl | 1.09$^3$ | >80$^3$ | >73.4 |
| 7 | N-pyrrolidine | 0.74$^3$ | >80$^3$ | >108.1 |
| 8 | N-piperidine | 1.75$^3$ | >80$^4$ | >45.7 |
| 9 | 4-hydroxy-N-piperidine | 2.02$^3$ | >80$^3$ | >39.6 |
| 10 | 4-fluoro-N-piperidine | 0.77$^3$ | >80$^2$ | >103.9 |
| 11 | 4-chloro-N-piperidine | 0.74$^3$ | >80$^2$ | >108.1 |
| 12 | 4-methyl-N-piperidine | 0.54$^3$ | >80$^3$ | >148.1 |
| 13 | 4,4-dimethyl-N-piperidine | 0.49$^3$ | >80$^3$ | >160 |

TABLE 1-continued

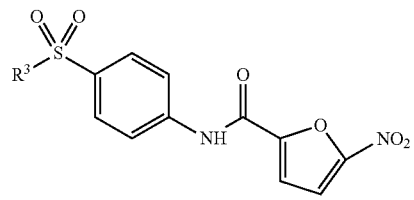

| Entry | R$^3$ | UPR CHOP Assay Potency$^a$ EC$_{50}$ (µM) | UPR XBP1 Assay Potency$^b$ EC$_{50}$ (µM) | Selectivity (XBP1/CHOP) x-fold |
|---|---|---|---|---|
| 14 | 4-tert-butyl-N-piperidine | 0.68$^3$ | >80$^2$ | >117.6 |
| 15 | 4-spirocyclohexyl-N-piperidine | 0.73$^3$ | >80$^2$ | >109.6 |

Potency is expressed as mean of replicates.
$^1$n = 2;
$^2$n = 3;
$^3$n = 4;
$^4$n = 6.
$^a$AID602434.
$^b$AID602416.

A number of symmetrical, 4-substituted piperidines were evaluated as replacements for the morpholine ring, as these would provide some insight into the texture of the SAR and were synthetically readily accessible. A polar, 4-hydroxyl group was tolerated without much fluctuation in CHOP or XBP1 potency, as compared to the unsubstituted piperidine (entries 8 (SID104222721) and 9 (SID117695373)). Single halogen atoms or a methyl group incorporated in the 4-position of the piperidine ring afforded analogs with good CHOP potency with EC$_{50}$ values in the 0.77-0.53 µM range while leaving XBP1 unperturbed. Increasing steric bulk and lipophilic character at that 4-position of the scaffold culminated in analog SID 117695374 (entry 13) with an EC$_{50}$=0.50 µM, no discernable XBP1 liability and with a ClogP of 3.6. Larger, branched substituents occupying the same 4-position, which incidentally also increased the lipophilic character of the corresponding compounds, modestly attenuated CHOP activity (entries 14-15).

This analysis further indicated that hit compound (entry 1; SID104222717), possessed an attractive preliminary profile with CHOP EC$_{50}$=2.02 µM and XBP1 EC$_{50}$>71 µM, thus providing a selectivity of 35-fold. Shielding the oxygen atom of the morpholine ring with methyl groups had a modest, if any, enhancing effect on the CHOP potency (entry 2). Replacement of the oxygen atom for an NH-group (entry 3; SID117695371), a modification done to evaluate the impact of shifting the hydrogen-donating character, resulted in dramatically reduced CHOP potency without affecting XBP1. Removing the nitrogen of the morpholine ring was tolerated, and stripping the moiety of heteroatoms generated a promising submicromolar boost in CHOP potency, again, without affecting XBP1 (entries 4 and 5 (SID117695375), respectively).

Several of the analogs derived from these changes were evaluated in secondary assays as they met the preliminary probe criteria for UPR-CHOP and UPR-XBP1 activity. Select compounds were assessed in a dose response manner for the ability to suppress proliferation in both the CHOP wild-type and CHOP knockout murine embryonic fibroblasts (−/− MEF KO CHOP)(Table 2). Ideally, active compounds would attenuate proliferation in the wild type cells while leaving the knockout cells unaffected, thus indicating that the observed activity was CHOP pathway specific.

TABLE 2

| Entry | Proliferation MEF wt CHOP | Proliferation -/- MEF KO CHOP | ClogP |
|---|---|---|---|
| 1 | NT | NT | 1.32 |
| 2 | NT | NT | 2.36 |
| 3 | NT | NT | 1.31 |
| 4 | NT | NT | 0.36 |
| 5 | NT | NT | 2.75 |
| 6 | NT | NT | 2.65 |
| 7 | NT | NT | 2.01 |
| 8 | 7.84 ± 1.20[1] | >20[3] | 2.57 |
| 9 | NT | NT | 0.48 |
| 10 | 17.50 ± 2.69[2] | >20[3] | 2.26 |
| 11 | 4.77 ± 1.05[3] | >20[3] | 2.70 |
| 12 | 4.57 ± 1.24[2] | 16.30 ± 0.99[2] | 3.09 |
| 13 | 3.02 ± 0.60[2] | 9.17 ± 3.34[2] | 3.61 |
| 14 | 1.36 ± 0.54[2] | 2.05 ± 0.29[2] | 4.41 |
| 15 | NT | NT | 4.56 |

Potency is expressed as mean of replicates.
[1] n = 2;
[2] n = 3;
[3] n = 4.
NT = not tested.

For those compounds which were tested, increasing antiproliferative effects correlated with increasing ClogP in wild-type cells; however, a similar trend in toxicity was also observed in the knockout cells. The 4-chloro-N-piperidine derivative (entry 11) proved to have the best profile with a CHOP wt $EC_{50}$=4.77 µM and no observed effect ($EC_{50}$>20 µM) on -/- MEF knockout cells.

Nitrofurans are a class of compounds characterized by a nitro functional group ($NO_2$) attached to a furan heterocycle. The nitro functionality is a 1,3-dipolar group with delocalized charge spread over three atoms. Although UPR activation was observed in xenografts, nitro features in drug scaffolds may reduce absorption and tissue penetration and aryl nitro groups are often quickly metabolized in the liver. Therefore, drugs containing this structural element are typically used topically or to treat infections that do not require tissue penetration such as cystitis (urinary tract infection) and diarrheal illnesses. While, a prodrug approach has been used to overcome some of the ADMET liabilities (Chung, et al. (2011) *Curr. Pharmaceut. Design* 17:3515-3526; Tangallapally, et al. (2007) *Curr. Top. Med. Chem.* 7:509-526), modification of the furan group was also carried out (Table 3).

TABLE 3

| Entry | R[3] | R[4] | UPR CHOP Assay Potency[a] $EC_{50}$ (µM) | UPR XBP1 Assay Potency[b] $EC_{50}$ (µM) | Selectivity (XBP1/CHOP) x-fold |
|---|---|---|---|---|---|
| 1 | morpholine | 5-nitro-2-furan | 2.28[2] | >80[3] | >35.1 |
| 2 | morpholine | 5-nitro-2-thiophene | 13.5[2] | >80[3] | 5.9 |
| 3 | morpholine | 2-thiophene | >80[2] | >80[3] | 1.0 |
| 4 | morpholine | Phenyl | >80[2] | >80[3] | 1.0 |
| 5 | morpholine | 4-nitrophenyl | >80[2] | >80[2] | 1.0 |
| 6 | 4,4-dimethyl-N-piperidine | 3-nitrophenyl | >80[2] | >80[1] | 1.0 |
| 7 | N-4,4-dimethyl-N-piperidine | 1-methyl-5-nitro-1H-2-imidazole | 77.52[2] | >80[1] | 1.0 |

Potency is expressed as mean of replicates.
[1] n = 2;
[2] n = 3;
[3] n = 4;
[4] n = 6.
[a] AID602434.
[b] AID602416.

Replacing the 5-nitro-2-furan with a bioisosteric 5-nitro-2-thiophene resulted in a 6-fold loss in CHOP potency (entry 2; SID 104222733). Removal of the nitro group from the 2-thiophene group afforded an analog devoid of any activity. Phenyl derivatives, with or without the nitro functionality, were not tolerated (entries 4-6). A nitroimidazole analog was also found to be inferior to the parent 5-nitro-2-furan moiety (entry 7). Based on these results, an attempt was made to remove or replace the nitro group while preserving the furan functionality (Table 4).

TABLE 4

| Entry | R[3] | R[5] | UPR CHOP Assay Potency[a] $EC_{50}$ (µM) | UPR XBP1 Assay Potency[b] $EC_{50}$ (µM) | Selectivity (XBP1/CHOP) x-fold |
|---|---|---|---|---|---|
| 1 | N-morpholine | $NO_2$ | 2.28[2] | >80[3] | >35.1 |
| 2 | N-morpholine | H | >80[2] | >80[3] | 1.0 |
| 3 | N-morpholine | Methyl | >80[2] | >80[3] | 1.0 |
| 4 | N-morpholine | Bromine | >80[2] | >80[3] | 1.0 |
| 5 | 4,4-dimethyl-N-piperidine | $CF_3$ | >80[2] | >80[1] | 1.0 |

Potency is expressed as mean of replicates.
[1] n = 3;
[2] n = 4;
[3] n = 6.
[a] AID602434.
[b] AID6022416.

Removal of or exchange of the nitro group for methyl, bromine, or trifluoromethyl appendages resulted in complete loss of CHOP activity.

The SAR analysis indicated that the nitrofuran moiety was necessary for activating the CHOP pathway and that changes to the sulfonamide appendage permitted modulation of the lipophilicity and CHOP potency without affecting XBP1. Several compounds were identified with submicromolar CHOP activity and no discernable XBP1 liability. Subsequent analysis to prove that the observed effects were CHOP-pathway-specific revealed that some of the active analogs were toxic to cells due to non-related CHOP pathways and this trended with increased lipophilicity. The overall profile of the 4-chloro-N-piperidine derivative (Table 1, entry 11) was of interest, as it possessed submicromolar CHOP activating potency and excellent selectivity against XBP1 ($EC_{50}$=0.74 µM, XBP1 $EC_{50}$>80 µM, selectivity >108.1×). Moreover, it demonstrated desirable CHOP-pathway selective toxicity with a CHOP wild-type $EC_{50}$=4.77 µM and no observed effect ($EC_{50}$>20 µM) on –/– MEF knockout cells. As such, this compound (ML291) was selected as a suitable probe with which further interrogation of the CHOP pathway could be explored.

EXAMPLE 4

Cellular Activity of ML291

It was determined whether ML291 and ML291 congeners would induce cell death (cytotoxicity as measured by ATPLite®, which measures production of ATP from living cells) in cells where these pathways are operant, but not activate them in the absence of the pathways. Using mouse embryonic fibroblast (MEF) cell lines engineered to have the wild-type apoptotic pathways intact (MEF with wild-type CHOP) and MEF cells where this pathway has been knocked-out (MEF with CHOP KO), it was demonstrated that ML291 did not non-specifically kill MEFs; however, ML291 did potently kill MEFs in the presence of an intact CHOP pathway (Table 5), thereby demonstrating activation of apoptotic pathways. In a separate series of experiments, it was estimated that the activator potency of ML291 in MEF wild-type CHOP was ~4.8 µM $EC_{50}$ (n=4), which compared favorably (~6-fold shift) with its potency in the CHO-K1 cell reporter assays (762 nM $EC_{50}$).

TABLE 5

| Compound | Average $IC_{50}$ (µM) | |
|---|---|---|
| | Wild-Type CHOP | CHOP KO |
| 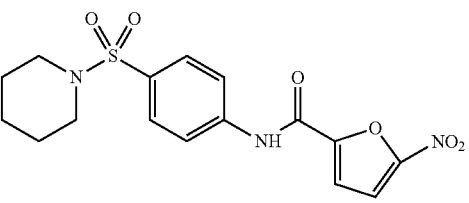 [SMILES: O=C(Nc1ccc(S(=O)(=O)N2CCCCC2)cc1)c1ccc([N+](=O)[O-])o1] | 7.84 ± 1.20 | >20 |
| 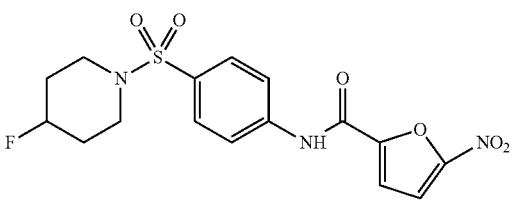 [SMILES: O=C(Nc1ccc(S(=O)(=O)N2CCC(F)CC2)cc1)c1ccc([N+](=O)[O-])o1] | 17.5 ± 2.69 | >20 |
| 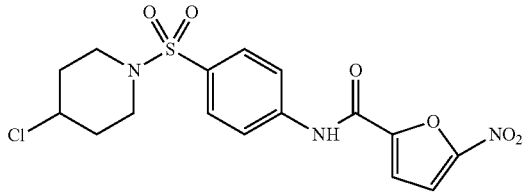 [SMILES: O=C(Nc1ccc(S(=O)(=O)N2CCC(Cl)CC2)cc1)c1ccc([N+](=O)[O-])o1] ML291 | 4.77 ± 1.05 | >20 |
| 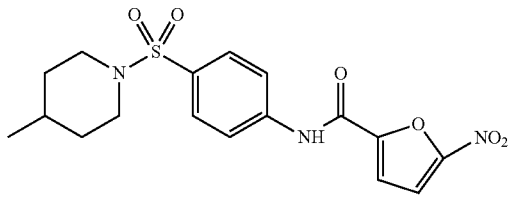 [SMILES: CC1CCN(S(=O)(=O)c2ccc(NC(=O)c3ccc([N+](=O)[O-])o3)cc2)CC1] | 4.57 ± 1.24 | 16.3 ± 0.99 |

TABLE 5-continued

| Compound | Average IC$_{50}$ (μM) | |
| --- | --- | --- |
| | Wild-Type CHOP | CHOP KO |
| 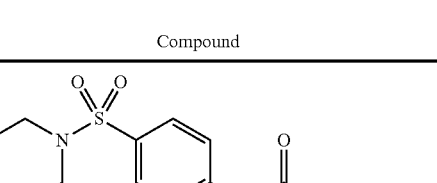 | 3.02 ± 0.60 | 9.17 ± 3.34 |
| 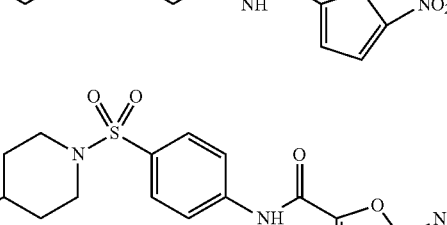 | 1.36 ± 0.54 | 2.05 ± 0.29 |

EXAMPLE 5

Profiling Assays

ML291 was evaluated in a detailed in vitro pharmacology screen. The results of this analysis are presented in Table 6.

TABLE 6

| | |
| --- | --- |
| Aqueous Solubility in pION's buffer (μg/mL) [μM]$^a$ pH 5.0/6.2/7.4 | 3.6/3.8/4.0 [8.7/9.2/9.7] |
| Aqueous Solubility in 1x PBS, pH 7.4 (μg/mL) [μM]$^a$ | 3.9 [9.4] |
| PAMPA Permeability, P$_e$ (×10$^{-6}$ cm/s) Donor pH: 5.0/6.2/7.4 Acceptor pH: 7.4 | 291/329/245 |
| Plasma Protein Binding   Human 1 μM/10 μM | 99.75/99.63 |
| (% Bound)                 Mouse 1 μM/10 μM | 84.47/84.35 |
| Plasma Stability (% Remaining at 3 hours @ 37° C.) Human/Mouse | 85.58/52.31 |
| Hepatic Microsome Stability (% Remaining after 1 hour @ 37° C.) Human/Mouse | 0.49/0.02 |
| Toxicity Towards Fa2N-4 Immortalized Human Hepatocytes LC$_{50}$ (μM) | 11.4 |

$^a$Solubility also expressed in molar units (μM) as indicated in italicized [bracketed values], in addition to more traditional μg/mL units.

ML291 had poor-to-modest solubility ranging from 8.7-9.7 μM (3.6-4.0 μg/mL) in aqueous buffers between a pH range of 5.2-7.4. Solubility was highest at the physiological of pH 7.4. This solubility was about 11-13 fold over its EC$_{50}$ (762 nM), so its apparent potency was not severely limited by its solubility.

The PAMPA (Parallel Artificial Membrane Permeability Assay) assay was used as an in vitro model of passive, transcellular permeability. An artificial membrane immobilized on a filter was placed between a donor and acceptor compartment. At the start of the test, drug was introduced in the donor compartment. Following the permeation period, the concentration of drug in the donor and acceptor compartments was measured using UV spectroscopy. ML291 exhibited good permeability at pHs of 5.0, 6.2 and 7.4 in the donor compartment, with highest permeability at pH 6.2.

Plasma protein binding is a measure of a drug's efficiency to bind to the proteins within blood plasma. The less bound a drug is, the more efficiently it can traverse cell membranes or diffuse. Highly plasma protein bound drugs are confined to the vascular space, thereby having a relatively low volume of distribution. In contrast, drugs that remain largely unbound in plasma are generally available for distribution to other organs and tissues. ML291 was highly plasma protein bound to human plasma proteins (>99%), though it is somewhat less tightly bound to mouse plasma proteins (~84%).

Plasma stability is a measure of the stability of small molecules and peptides in plasma and is an important parameter, which strongly can influence the in vivo efficacy of a test compound. Drug candidates are exposed in plasma to enzymatic processes (proteinases, esterases), and they can undergo intramolecular rearrangement or bind irreversibly (covalently) to proteins. ML291 appeared to be moderately stable in human plasma (~84% remaining), but less so in mouse plasma (~52% remaining).

The microsomal stability assay is commonly used to rank compounds according to their metabolic stability. This assay addresses the pharmacologic question of how long the parent compound will remain circulating in plasma within the body. ML291 was almost completely metabolized in both human and mouse liver homogenates within 1 hour.

ML291 was submitted to Ricerca Biosciences LLC (Bothell, Wash.) to evaluate it in radio-ligand binding assays to determine activity against a panel of 67 GPCRs, ion channels and transporters at 10 μM. ML291 only scored as having significant activity (68% inhibition) against the dopamine transporter (DAT), so it did not appear to be generally promiscuous compound with respect to these receptors.

EXAMPLE 6

Mechanism of Action Analyses

While ML291 robustly and selectively. activated the apoptotic (CHOP) arm of UPR in the engineered luciferase reporter CHO-K1 cells, while not activating reporter under the control of the adaptive arm (XBP1) promoters, direct confirmation of the selective activation of genes and pathways on the apoptotic UPR arm in a biologically relevant cell or cell line was needed. To determine whether or not ML291 could selectively activate the apoptotic (CHOP) arm of the UPR, relevant oral squamous cell carcinoma cell lines, UMSCC23, A253 and HN12, were treated with ML291 for four hours. The activation/induction of associated genes along the UPR sub-pathways were measured by quantitative real-time reverse-transcription PCR (qRT-PCR) analysis of cDNA pools generated from whole cell lysates. These transcription profile studies revealed a 5-fold selectivity of CHOP transcripts (apoptotic) compared to spliced XBP1 (adaptive). Furthermore, the simultaneous induction of the CHOP down stream target GADD34, but not the DNA excision and repair gene ERCC1 indicated ML291 was activating CHOP via the UPR and not DNA damage. This analysis further revealed an accumulation of CHOP, GADD34 and spliced XBP1 transcripts (FIG. 1). Immunoblot analysis of whole cell lysates revealed an accumulation of CHOP, ATF4, GADD34 and the phosphorylated form of eIF2α (p-eIF2α), a hallmark of ER stress, supporting the gene expression assays. Identically treated cells demonstrated an accumulation of ubiquitinated proteins indicating the cells were working to resolve a burden of unfolded proteins through the ubiquitin-proteasome system. These data definitively show that ML291 can selectively activate CHOP via a mechanism governed by the UPR apoptotic arm. These data, coupled with the observation that ML291-treated MEF cells, with intact wild-type CHOP, undergo apoptosis while ML291-treated −/−MEF cells (CHOP knock-out) show lack of cytotoxicity, indicate that ML291 may selectively activate apoptotic pathways in tumors thereby leading to their selective and efficacious killing.

EXAMPLE 7

Animal Model of Oral Squamous Cell Carcinoma

Stable oral squamous cell carcinoma (OSCC) cell lines that express luciferase constructs for XBP1 and human CHOP were generated. The XBP1 cell line (UMSCC23-XBP1-luc) was generated with the same XBP1 plasmid used to make the CHO-XBP1 cell line used in the primary assay. The CHOP cell line (UMSCC23-hCHOP-luc) was generated with a novel plasmid created by cloning ~3 kb of the human CHOP promoter to a luciferase gene. The Chop promoter driving the expression of luciferase in the CHO cell line used for screening was murine; the 26 bp intron that is spliced from XBP1 (by IRE1α) is conserved between murine and human. Single high-expressing clones were identified and used successfully to create xenografts (in SCID mice) that express luciferase when stimulated with tunicamycin or other UPR-inducing compounds. Using this model, the ability of ML291 to activate the UPR (i.e., CHOP gene activation and/or XBP1 mRNA splicing) can be observed in vivo in real-time. Additionally, the ability of ML291 to reduce tumor burden or interfere with tumor growth can be quantitatively measured over time. In vivo luminescence was analyzed by IP injection of luciferin and imaging on a CARESTREAM In-Vivo Xtreme multi-modal optical and X-ray small animal imaging system. Bioluminescent images of xenografts made with the stable OSCC cell line A253-CHOP-luc demonstrated increased luminescence 24 hours after a 10 mg/kg (IP) dose of ML291. Immunoblots with tumor lysate demonstrated increased BiP, CHOP and also p-eIF2α. These data indicate that ML291 induces ER stress and the UPR in vivo.

To confirm the ability of ML291 to activate UPR-luciferase reporters stably transfected into UMSCC23 and A253 cells and reduce tumor burden, additional xenograft studies are performed with additional animals to permit real-time measurement of UPR activation during drug treatment (bioluminescent imaging). The data presented herein indicate that ML291 can activate the UPR in xenograft tissue at 10 mg/kg. However, pharmacokinetic studies (IV and IP) suggest that further chemical optimization might improve activity. Thus, mice are injected IP in the morning with 10-100 mg/kg ML291. Injection in the morning, i.e., when the lights come on in the vivarium and the mice stomachs are most likely to be full, is a technique known to enhance absorption of nitrofurans into the bloodstream (Heinrichs (2001) *Behavioural Brain Res.* 125:81-88). Preliminary experiments revealed no differences in weight, physical appearance, disposition or activity between mice that were IP injected with 10 mg/kg ML291 daily and controls. Upon completion of this experiment, control and ML291 treated mice (3 each) undergo complete pathological necropsy to identify gross or histological signs of organ toxicity. Once the degree to which ML291 induces the UPR and reduces xenograft burden is analyzed, additional studies are carried out with combination therapies using standard of care OSCC drugs. Preliminary combination studies with cisplatin and taxol demonstrated reduced $IC_{50}$ values for ML291 and enhanced toxicity. It is posited that ML291-enforced UPR in the tumor milieu potentiates conventional therapies and might enhance the effects of cisplatin, ifosfamide or taxol.

EXAMPLE 8

Apoptotic Cell Death in OSCC and Ovarian Cancer Cells

Figure 3A:
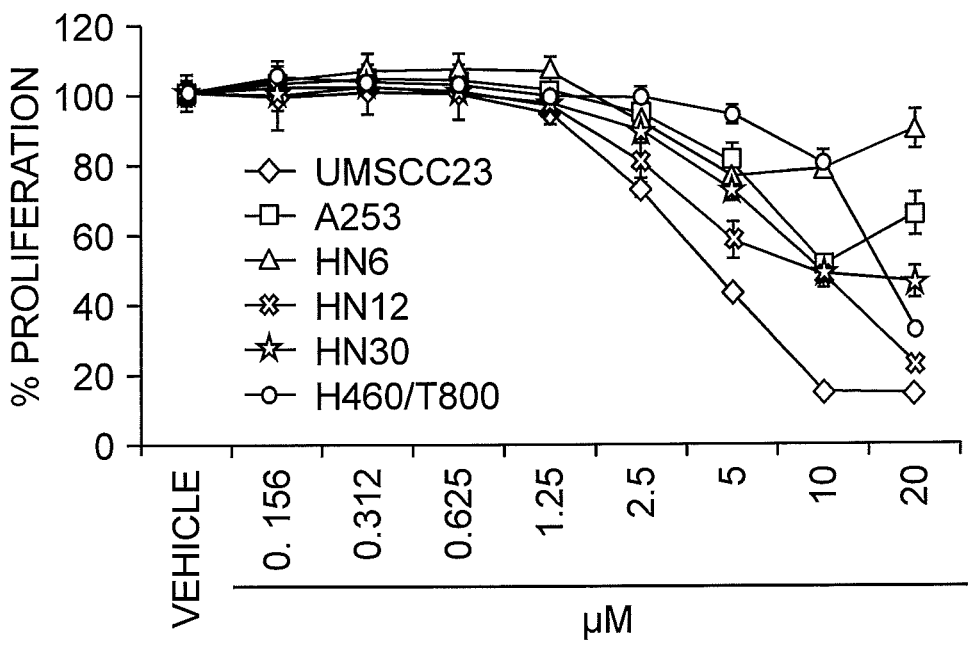
FIG. 3A and FIG. 3B show that ML291 inhibits proliferation and induces apoptosis.
Figure 3B:
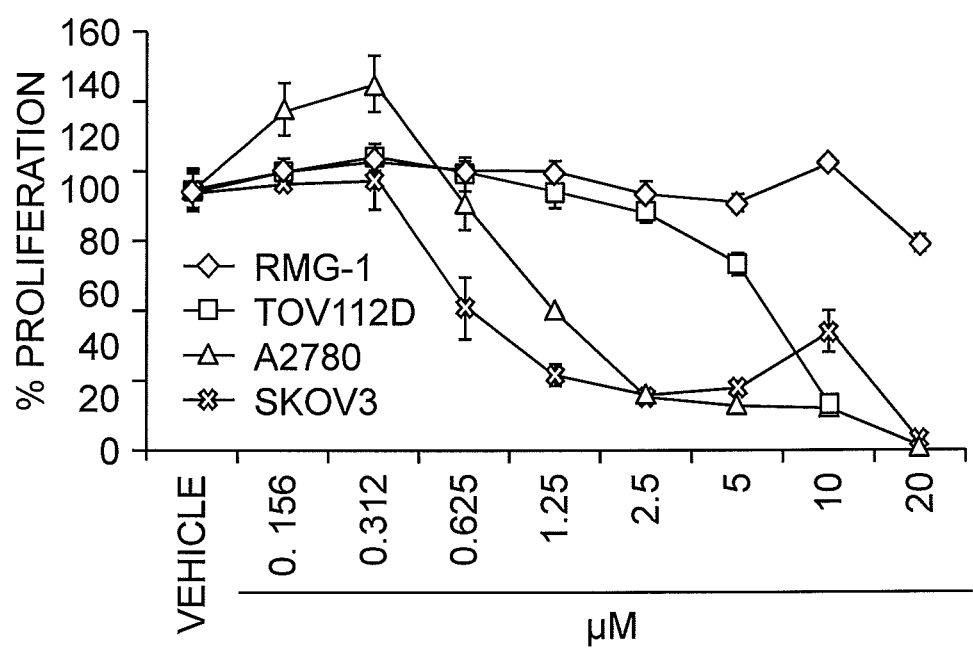

To determine whether ML291 could reduce the proliferation of malignant cells, a panel of OSCC (UMSCC23, A253, HN6, HN12, HN30, H460/T800) and ovarian cancer (RMG-1, TOV112D, A2780 and SKOV3) cell lines, were treated with increasing doses (0.15-20 µM) of ML291 for 24 hours (FIGS. 3A and 3B). ML291 reduced proliferation in eight of the ten cell lines demonstrating $IC_{50}$ values 1.6-18.9 µM (Table 7).

TABLE 7

| Cell Line | Average $IC_{50}$ (µM) |
|---|---|
| UMSCC23 | 7.31 ± 1.68* |
| A253 | 17.2 ± 3.64* |
| HN6 | >20* |
| HN12 | 7.17 ± 0.69* |
| HN30 | 8.95 ± 1.06* |
| H460/T800 | 18.9 ± 1.83* |
| RMG-1 (ovarian) | >20 |
| TOV112D (ovarian) | 6.59 |
| A2780 (ovarian) | 2.16 |
| SKOV3 | 1.59 |

*Average of three experiments.

Although primary or non-malignant cells were not examined, the fact that two cell lines were resistant (up to 20 µM), and pharmacokinetic studies with animals injected bi-weekly with 10 mg/kg for four weeks did not display any obvious side effects, indicates that ML291 is not generally cytotoxic.

To identify genes that confer resistance to apoptotic UPR signaling and to further elucidate the mechanisms by which this novel chemical series induces a terminal UPR, a genome-wide RNAi screen in OSCC cells is performed. This approach employs a pool of ~200,000 HIV-based viruses that target the entire human genome with at least 5 unique shRNA sequences per gene. Pooled infected cells are puro-selected and treated with 10 μM ML291 (i.e., the IC$_{50}$ dose) or vehicle for 24 hours. Genomic DNA is collected from half of the cells, the other half is expanded and re-exposed to ML291 or vehicle for another 24 hours and genomic DNA is collected. Genomic DNA from the ML291-surviving and vehicle-treated cells is hybridized to an AFFYMETRIX Human Genome U133 Plus 2.0 Array to identify genes able to interfere with ML291-induced cytotoxicity. It has been reported that double selection results in a 300-fold enrichment in target effected genes identified through shRNA screening (Bassik, et al. (2009) Nat. Meth. 6:443-445). The shRNA sequences hybridize to the array in a fashion that the count of hits for a specific gene corresponds to the number of cells surviving with that specific shRNA. To confirm the results of the shRNA screen lentiviruses that express specific shRNA's or pools of siRNA's in a panel of human cancers are used. Alternatively, or in addition to, targeted genome editing can be used to knockout any gene in the genome with highly active TALEN's of Zinc Finger Nucleases.

To determine if apoptosis might contribute to ML291-reduced proliferation, immunoblot experiments were performed with three OSCC cell lines. Pro-caspase 9 levels were decreased by 8 hours, an affect that was followed by accumulation of Caspase 3 and cleaved PARP. NOXA, PUMA, BAK and BAX levels increased during the same time course, implicating the pro-apoptotic BH3-only BCL2 family in ML291 proliferation inhibition.

qRT-PCR profiling with HN12 cells identified 17 apoptosis-related genes that were upregulated following ML291 treatment including BAX, BCL10, BIRC2, CARD6, CARD8, CASP9, CD40, CRADD, DAPK1, DFFA, FAS, FASLG, TNF, TNFSF10, CD70, TP53BP2 and TP73.

Figure 2:
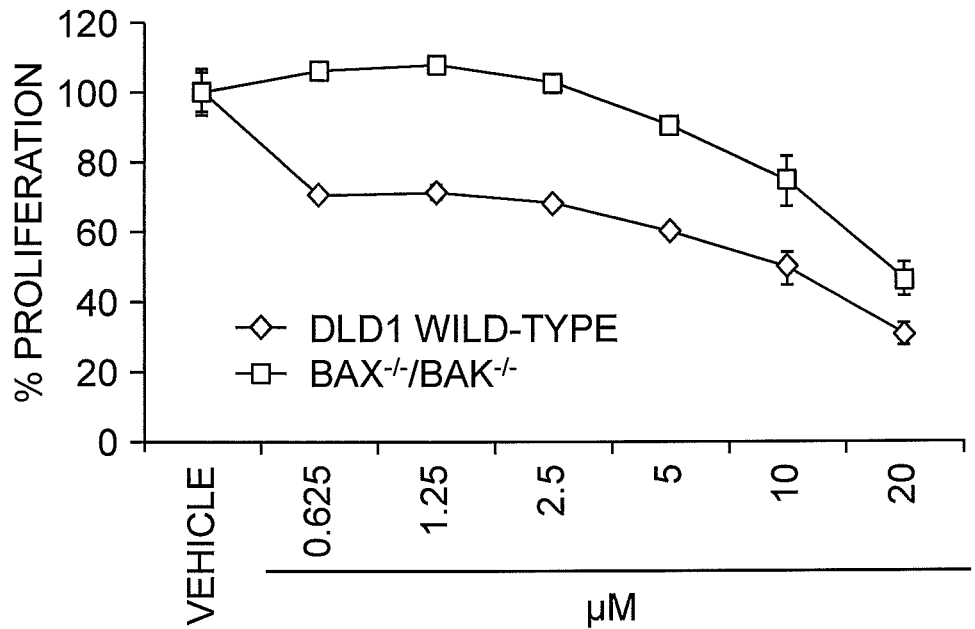
FIG. 2 shows that Bax/Bak knockout cells are more resistant to ML291 than wild-type cells.

Furthermore, the human Zinc Finger Nuclease-deleted colorectal cell line DLD1(BAX$^{-/-}$)(BAK$^{-/-}$) was significantly more able to withstand ML291 exposure than wild-type controls (FIG. 2). These data indicate that ML291 can induce apoptosis and reduce the proliferation of OSCC cells in culture.

EXAMPLE 9

Synthesis and Physical Properties of ML291

The IUPAC name of the probe ML291 is N-(4-((4-chloropiperidin-1-yl)sulfonyl)phenyl)-5-nitrofuran-2-carboxamide.

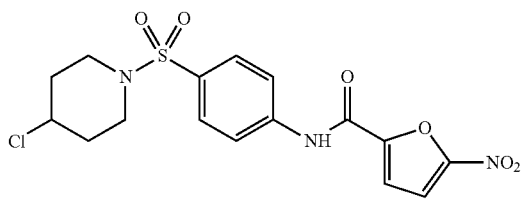

ML291

The physiochemical data for ML291 is presented in Table 8.

TABLE 8

| Molecular Formula | $C_{16}H_{16}ClN_3O_6S$ |
| --- | --- |
| Molecular Weight | 413.83 g/mol |
| Exact Mass | 413.04 g/mol |
| CLogP | 2.70 |
| Topological Polar Surface Area | 127.52 |
| Physical State | Off-White Solid |
| Melting Point | 228-232° C. |

Structure Verification and Purity. $^1$H and $^{13}$C NMR spectra were recorded on a Bruker AM 400 spectrometer (operating at 400 and 101 MHz, respectively) or a Bruker AVIII spectrometer (operating at 500 and 126 MHz, respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. Liquid chromatography-mass spectrometry (LCMS) analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 μm column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3H-tetrafluoropropoxy) phosphazine; and a make-up solvent of 90:10:0.1 MeOH:Water:Formic Acid, which was introduced to the LC flow prior to the source to assist ionization. Melting points were determined on a Stanford Research Systems OptiMelt apparatus.

The probe was prepared as depicted in Scheme 2.

SCHEME 2

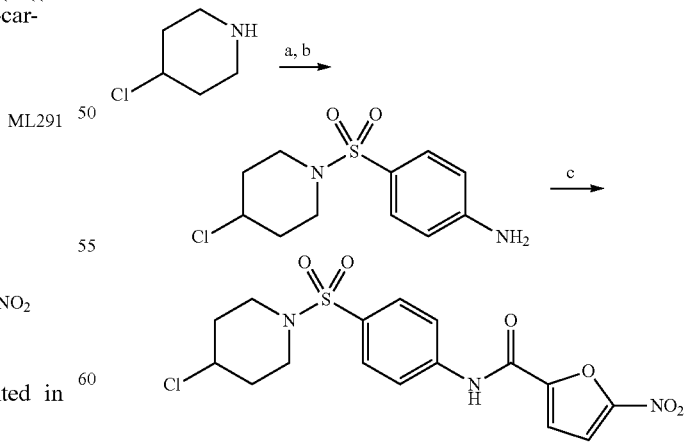

Reagents: (a) 4-nitrobenzene-1-sulfonyl chloride, pyridine, THF, 60° C., 20 min; (b) Raney Ni, NaBH$_4$, CH$_3$OH/CH$_2$Cl$_2$, 0° C., 30 min;
c) 5-nitrofuran-2-carbonyl chloride, CH$_3$CN, 150° C., μw, 20 min.

4-Chloro-1-((4-Nitrophenyl)Sulfonyl)Piperidine

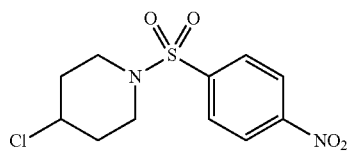 [SMILES: O=[N+]([O-])c1ccc(S(=O)(=O)N2CCC(Cl)CC2)cc1]

To a vial was added 4-nitrobenzenesulfonyl chloride (0.32 g, 1.4 mmol), pyridine (0.11 g, 1.4 mmol) and THF (1.5 mL). The reaction was stirred at room temperature while 4-chloropiperidine (0.13 g, 1.0 mmol) was added drop-wise over 10 minutes. The reaction was subsequently heated to 60° C. for 20 minutes and monitored by thin layer chromatography (TLC). Upon completion, the reaction was cooled to room temperature, diluted with EtOAc (10 mL) and washed with saturated aq. $NaHCO_3$ (10 mL). The EtOAc layer was separated, dried with $MgSO_4$, filtered, adsorbed to silica and purified by silica gel flash column chromatography (15 minutes, 0-30% v/v EtOAc/hexanes) to produce pure 4-chloro-1-((4-nitrophenyl)sulfonyl)piperidine (0.29 g, 0.96 mmol, 96% yield). $^1$H NMR (400 MHz, $CDCl_3$): δ 8.40 (d, J=9.0 Hz, 2H), 7.96 (d, J=9.0 Hz, 2H), 4.22 (m, 1H), 3.29 (m, 2H), 3.18 (m, 2H), 2.16 (m, 2H), 1.97 (m, 2H).

4-((4-Chloropiperidin-1-yl)Sulfonyl)Aniline

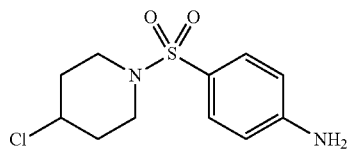

To a vial containing 4-chloro-1-((4-nitrophenyl)sulfonyl) piperidine (0.29 g, 0.96 mmol) was added 1:1 MeOH:$CH_2Cl_2$ (3 mL:3 mL), and the reaction was cooled to 0° C. Raney nickel (0.006 g, 0.096 mmol) was added followed by portion-wise addition of sodium borohydride (0.073 g, 1.9 mmol). Once addition was complete, the reaction mixture was stirred at 0° C. for 30 minutes and was then diluted with $CH_2Cl_2$ (10 mL) and filtered slowly. The $CH_2Cl_2$ layer was washed with water (10 mL), separated, dried with $MgSO_4$, filtered, adsorbed to silica and purified by silica gel flash column chromatography (15 minutes, 0-5% v/v MeOH/DCM) to produce pure 4-((4-chloropiperidin-1-yl)sulfonyl) aniline (0.23 g, 0.82 mmol, 86% yield). $^1$H NMR (400 MHz, $CDCl_3$): δ 7.66 (d, J=8.7 Hz, 2H), 7.06 (d, J=8.6 Hz, 2H), 7.03 (s, 1H), 5.32 (s, 1H), 4.12 (m, 1H), 3.16 (m, 2H), 3.10 (m, 2H), 2.13 (m, 2H), 1.95 (m, 2H).

N-(4-((4-Chloropiperidin-1-yl)Sulfonyl)Phenyl)-5-Nitrofuran-2-Carboxamide (ML291). To a microwave vial was added 4-((4-chloropiperidin-1-yl)sulfonyl)aniline (0.23 g, 0.82 mmol), 5-nitro-2-furoyl chloride (0.16 g, 0.90 mmol) and acetonitrile (3 mL). The vial was sealed and heated to 150° C. in the microwave for 20 minutes. The reaction then cooled to room temperature and was diluted with $CH_2Cl_2$ (10 mL) and washed with saturated $NaHCO_3$ (10 mL). The $CH_2Cl_2$ layer was separated, dried with $MgSO_4$, filtered and adsorbed to silica gel. The crude product was purified by silica gel flash column chromatography (20 minutes, 0-5% v/v MeOH/$CH_2Cl_2$) to produce pure N-(4-((4-chloropiperidin-1-yl)sulfonyl)phenyl)-5-nitrofuran-2-carboxamide, ML291 (0.11 g, 0.26 mmol, 31% yield). $^1$H NMR (400 MHz, DMSO-$d_6$): δ 11.01 (s, 1H), 8.03 (d, J=8.8 Hz, 2H), 7.83 (d, J=3.9 Hz, 1H), 7.79 (d, J=8.8 Hz, 2H), 7.70 (d, J=3.9 Hz, 1H), 4.27 (m, 1H), 3.17 (m, 2H), 2.87 (m, 2H), 2.10 (m, 2H), 1.79 (m, 2H). $^{13}$C NMR (100 MHz, DMSO-$d_6$): δ 154.9, 151.9, 147.3, 142.2, 130.4, 128.6, 120.4, 117.2, 113.4, 56.1, 43.4, 33.9. LCMS retention time: 3.147 min. LCMS Purity at 214 nm: 97.5%. HRMS: m/z calcd for $C_{16}H_{17}ClN_3O_6S$ (M+H$^+$) 414.0521, found 414.0522. Melting point: 228-232° C.

Solubility. Solubility was measured in phosphate-buffered saline (PBS) at room temperature (23° C.). PBS by definition is 137 mM NaCl, 2.7 mM KCl, 10 mM sodium phosphate dibasic, 2 mM potassium phosphate monobasic and a pH of 7.4. Probe ML291 was found to have a solubility measurement of 3.9 μg/mL, or 9.4 μM, under these conditions.

Stability. Stability was measured under two distinct conditions with ML291: at room temperature (23° C.) in PBS (no antioxidants or other protectants and DMSO concentration below 0.1%) and with 50% acetonitrile added to account for challenges with solubility of the compound in PBS alone. Stability was determined as the loss of compound with time over a 48 hour period with a minimum of 6 time points. The percent remaining compound at the end of the 48 hours indicated that, with no additives, 11.44% of ML291 remained after 48 hours; however, this data was dependent on the solubility limitations in PBS buffer. With the addition of 50% acetonitrile, to account for solubility, 100% of ML291 remained after 48 hours.

EXAMPLE 10

Synthesis of ML291 Analogs

The high throughput screen identified a first-in-class, potent (760 nM $EC_{50}$), not generally cytotoxic, submicromolar potent chemical probe, ML291, that selectively activates the apoptotic but not the adaptive arm of the UPR, and that moreover demonstrates efficacy in inducing cell death through activation of the apoptotic in relevant cells. Given that the SAR analysis indicated that the nitro moiety on the furan ring was required for its activating activity, and may be the reason for ML291's modest plasma stability and microsomal instability, analogs of ML291 were prepared, which contained the nitro moiety on the furan ring.

ML291 and analogs thereof were generally synthesized by the method shown in Scheme 3. Commercially available 4-substituted piperidines 1a-d were treated with an aryl sulfonyl chloride to afford the corresponding sulfonamides which were subsequently reduced to reveal the anilines 2a-d. Conversion to the final products 3a-f was accomplished by treating anilines 2a-f with 5-nitrofuran acyl chloride under microwave irradiation to generate the final compounds 3a-f.

SCHEME 3

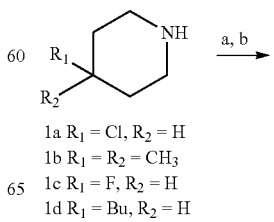

1a $R_1$ = Cl, $R_2$ = H
1b $R_1$ = $R_2$ = $CH_3$
1c $R_1$ = F, $R_2$ = H
1d $R_1$ = Bu, $R_2$ = H

-continued

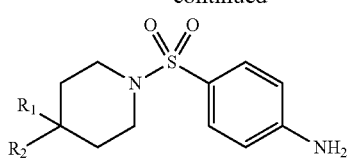

2a R₁ = Cl, R₂ = H
2b R₁ = R₂ = CH₃
2c R₁ = F, R₂ = H
2d R₁ = tBu, R₂ = H
2e R₁ = R₂ = H
2f R₁ = CH₃, R₂ = H

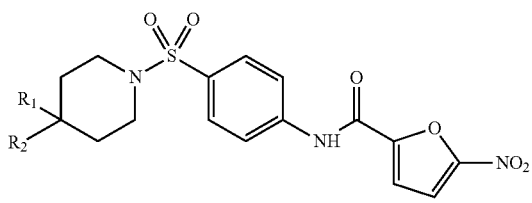

3a R₁ = Cl, R₂ = H
3b R₁ = R₂ = CH₃
3c R₁ = F, R₂ = H
3d R₁ = tBu, R₂ = H
3e R₁ = R₂ = H
3f R₁ = CH₃, R₂ = H

Reagents: (a) 4-nitrobenzene-1-sulfonyl chloride, pyridine, THF, 60° C., 20 min; (b) Raney Ni, NaBH₄, CH₃OH/CH₂Cl₂, 0° C., 30 min; c) 5-nitrofuran-2-carbonyl chloride, CH₃CN, 150° C., μW, 20 min.

N-(4-((4,4-Dimethylpiperidin-1-yl)Sulfonyl)Phenyl)-5-Nitrofuran-2-Carboxamide (SID 134228470; CID 51035286)

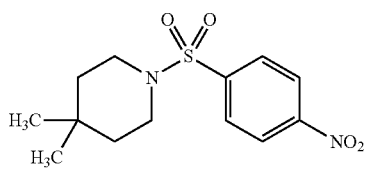 [SMILES: CC1(C)CCN(S(=O)(=O)c2ccc([N+](=O)[O-])cc2)CC1]

4,4-dimethyl-1-((4-nitrophenyl)sulfonyl)piperidine was prepared by combining 4-nitrobenzenesulfonyl chloride (0.23 g, 1.0 mmol), pyridine (0.12 g, 1.6 mmol) and THF (3 mL). The reaction mixture was stirred at room temperature while 4,4-dimethylpiperidine (0.15 g, 1.2 mmol) was added drop-wise over 10 minutes. The reaction was subsequently heated to 60° C. for 20 minutes and monitored by TLC. Upon completion, the reaction cooled to room temperature, was diluted with EtOAc (10 mL) and washed with saturated NaHCO₃ (10 mL). The EtOAc layer was separated and dried with MgSO₄, filtered, adsorbed to silica and purified by silica gel flash column chromatography (15 minutes, 0-30% v/v EtOAc/hexanes) to produce pure 4,4-dimethyl-1-((4-nitrophenyl)sulfonyl)piperidine (0.25 g, 0.84 mmol, 81% yield). ¹H NMR (400 MHz, CDCl₃): δ 8.39 (d, J=9.0 Hz, 2H), 7.96 (d, J=9.0 Hz, 2H), 3.07 (t, J=5.7 Hz, 4H), 1.46 (t, J=5.8 Hz, 4H), 0.86 (s, 6H).

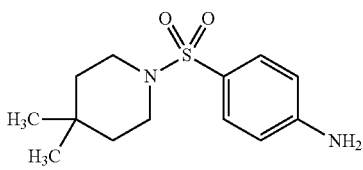 [SMILES: CC1(C)CCN(S(=O)(=O)c2ccc(N)cc2)CC1]

4-((4,4-dimethylpiperidin-1-yl)sulfonyl)aniline: The 4,4-dimethyl-1-((4-nitrophenyl)sulfonyl) piperidine (0.12 g, 0.40 mmol) was added to a vial and with MeOH:DCM (3 mL:1 mL) and the reaction was cooled to 0° C. The Raney Nickel (0.002 g, 0.040 mmol) was added followed by portion-wise addition of sodium borohydride (0.030 g, 0.80 mmol). The reaction was stirred at 0° C. for 30 minutes and was then diluted with CH₂Cl₂ (10 mL) and filtered slowly. The CH₂Cl₂ layer was washed with water (10 mL), dried with MgSO₄, filtered, adsorbed to silica and purified by silica gel flash column chromatography (15 minutes, 0-5% v/v MeOH/CH₂Cl₂) to produce pure 4-((4,4-dimethylpiperidin-1-yl)sulfonyl)aniline (0.11 g, 0.39 mmol, 98% yield). ¹H NMR (400 MHz, CDCl₃): δ 7.35 (d, J=8.7 Hz, 2H), 6.64 (d, J =8.6 Hz, 2H), 6.03 (s, 2H), 2.80 (t, J=5.6 Hz, 4H), 1.34 (t, J=5.7 Hz, 4H), 0.78 (s, 6H).

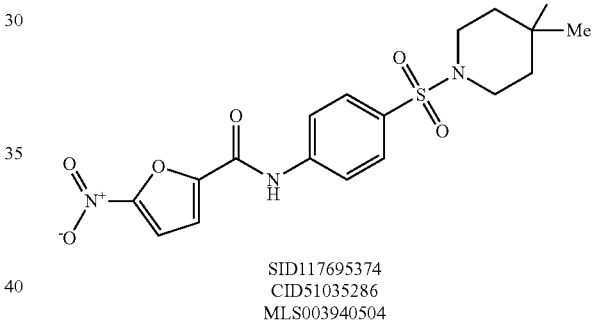

SID117695374
CID51035286
MLS003940504

N-(4-((4,4-dimethylpiperidin-1-yl)sulfonyl)phenyl)-5-nitrofuran-2-carboxamide. To a microwave vial was added 4-((4,4-dimethylpiperidin-1-yl)sulfonyl)aniline (0.11 g, 0.39 mmol), 5-nitro-2-furoyl chloride (0.076 g, 0.44 mmol) and acetonitrile (3 mL). The vial was sealed and heated to 150° C. in the microwave for 20 minutes. The reaction was cooled to room temperature and was diluted with CH₂Cl₂ (10 mL) and washed with saturated NaHCO₃ (10 mL). The CH₂Cl₂ layer was separated, dried with MgSO₄, filtered and adsorbed to silica gel. The crude product was purified by silica gel flash column chromatography (20 minutes, 0-5% v/v MeOH/CH₂Cl₂) to produce pure N-(4-((4,4-dimethylpiperidin-1-yl)sulfonyl)phenyl)-5-nitrofuran-2-carboxamide (0.10 g, 0.25 mmol, 63% yield). ¹H NMR (400 MHz, DMSO-d₆): δ 10.99 (s, 1H), 8.02 (d, J=8.9 Hz, 2H), 7.84 (d, J=3.9 Hz, 1H), 7.78 (d, J=8.8 Hz, 2H), 7.71 (d, J=3.9 Hz, 1H), 2.91 (t, J=5.5 Hz, 4H), 1.36 (t, J=5.6 Hz, 4H), 0.79 (s, 6H). ¹³H NMR (100 MHz, DMSO-d₆): δ 155.0, 151.9, 147.3, 141.9, 130.8, 128.5, 120.3, 117.2, 113.4, 42.3, 37.1, 27.8, 27.1. LCMS retention time: 3.307 min. LCMS Purity at 214 nm: 98.3%. HRMS: m/z calcd for $C_{18}H_{22}N_3O_6S$ (M+H⁺) 408.1224, found 408.124. Melting point: 145-150° C.

N-(4-((4-Fluoropiperidin-1-yl)Sulfonyl)Phenyl)-5-Nitrofuran-2-Carboxamide

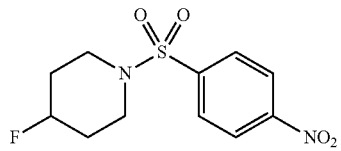

4-fluoro-1-((4-nitrophenyl)sulfonyl)piperidine: To a vial was added 4-nitrobenzenesulfonyl chloride 2 (0.13 g, 0.58 mmol), pyridine (0.12 g, 1.5 mmol) and THF (2 mL). The reaction was stirred at room temperature while 4-fluoropiperidine HCl (0.097 g, 0.70 mmol) was added over 10 minutes. The reaction was subsequently heated to 60° C. for minutes and monitored by TLC. Upon completion, the reaction was cooled to room temperature, was diluted with EtOAc (10 mL) and washed with saturated NaHCO$_3$ (10 mL). The EtOAc layer was separated, dried with MgSO$_4$, filtered, adsorbed to silica and purified by silica gel flash column chromatography (15 minutes, 0-30% v/v EtOAc/hexanes) to produce pure 4-fluoro-1-((4-nitrophenyl)sulfonyl)piperidine (0.15 g, 0.52 mmol, 89% yield). $^1$H NMR (400 MHz, CDCl$_3$): δ 8.45 (d, J=9.0 Hz, 2H), 8.03 (d, J=8.9 Hz, 2H), 4.83-4.68 (m, 1H), 3.15 (m, 2H), 2.97 (m, 2H), 1.98-1.78 (m, 4H).

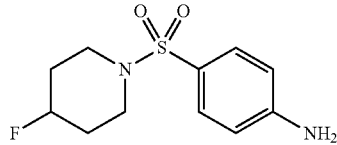 [SMILES: Nc1ccc(S(=O)(=O)N2CCC(F)CC2)cc1]

4-((4-fluoropiperidin-1-yl)sulfonyl)aniline. The 4-fluoro-1-((4-nitrophenyl)sulfonyl)piperidine (0.15 g, 0.52 mmol) was added to a vial and with MeOH:CH$_2$Cl$_2$ (3 mL:1 mL) and the reaction was cooled to 0° C. The Raney Nickel (0.003 g, 0.052 mmol) was added, followed by portion-wise addition of sodium borohydride (0.039 g, 1.0 mmol). The reaction stirred at 0° C. for 30 minutes and was then diluted with CH$_2$Cl$_2$ (10 mL) and filtered slowly. The CH$_2$Cl$_2$ layer was washed with water (10 mL), separated, dried with MgSO$_4$, filtered, adsorbed to silica and purified by silica gel flash column chromatography (15 minutes, 0-5% v/v MeOH/DCM) to produce pure 4-((4-fluoropiperidin-1-yl)sulfonyl)aniline (0.13 g, 0.51 mmol, 98% yield). $^1$H NMR (400 MHz, CDCl$_3$): δ 7.36 (d, J=8.7 Hz, 2H), 6.64 (d, J=8.7 Hz, 2H), 6.08 (s, 2H), 4.79-4.64 (m, 1H), 2.94 (m, 2H), 2.80 (m, 2H), 1.93-1.72 (m, 4H).

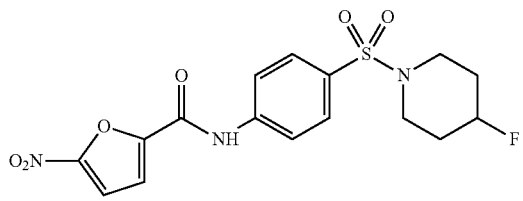 [SMILES: O=C(Nc1ccc(S(=O)(=O)N2CCC(F)CC2)cc1)c1ccc([N+](=O)[O-])o1]

N-(4-((4-fluoropiperidin-1-yl)sulfonyl)phenyl)-5-nitrofuran-2-carboxamide. To a microwave vial was added 4-((4-fluoropiperidin-1-yl)sulfonyl)aniline (0.039 g, 0.15 mmol), 5-nitro-2-furoyl chloride (0.029 g, 0.17 mmol) and acetonitrile (3 mL). The vial was sealed and heated to 150° C. in microwaves for 20 minutes. The reaction was then cooled to room temperature and was diluted with CH$_2$Cl$_2$ (10 mL) and washed with saturated NaHCO$_3$ (10 mL). The CH$_2$Cl$_2$ layer was separated, dried with MgSO$_4$, filtered and adsorbed to silica gel. The crude product was purified by silica gel flash column chromatography (20 minutes, 0-5% v/v MeOH/CH$_2$Cl$_2$) to produce pure N-(4-((4-fluoropiperidin-1-yl)sulfonyl)phenyl)-5-nitrofuran-2-carboxamide (0.030 g, 0.076 mmol, 49% yield). $^1$H NMR (400 MHz, DMSO-d$_6$): δ 11.02 (s, 1H), 8.04 (d, J=8.9 Hz, 2H), 7.84 (d, J=3.9 Hz, 1H), 7.80 (d, J=8.8 Hz, 2H), 7.73 (d, J=4.0 Hz, 1H), 4.82-4.68 (m, 1H), 3.07 (m, 2H), 2.94 (m, 2H), 1.98-1.78 (m, 4H). $^{13}$H NMR (100 MHz, DMSO-d$_6$): δ 155.1, 152.0, 147.4, 142.4, 130.2, 128.7, 120.5, 117.3, 113.4, 86.8 (d, J=163.5 Hz), 42.2 (d, J=12.6), 30.1 (d, J=32.4 Hz). LCMS retention time: 3.001 min. LCMS Purity at 214 nm: 96.7%. HRMS: m/z calcd for C$_{16}$H$_{17}$N$_3$O$_6$S (M+H$^+$) 398.0817, found 398.0845. Melting point: 228-232° C.

N-(4-((4-tert-butylpiperidin-1-yl)sulfonyl)phenyl)-5-nitrofuran-2-carboxamide

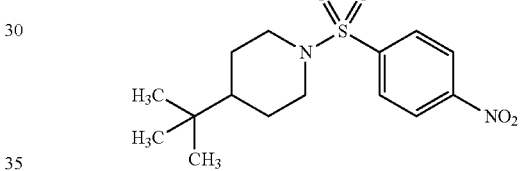

4-tert-butyl-1-((4-nitrophenyl)sulfonyl)piperidine: To a vial was added 4-nitrobenzenesulfonyl chloride 2 (0.20 g, 0.91 mmol), pyridine (0.22 g, 2.7 mmol) and THF (4 mL). The reaction was stirred at room temperature while 4-tert-butylpiperidine HCl (0.16 g, 0.91 mmol) was added over 10 minutes. The reaction was subsequently heated to 60° C. for 20 minutes and monitored by TLC. Upon completion, the reaction cooled to room temperature, was diluted with EtOAc (10 mL) and washed with saturated NaHCO$_3$ (10 mL). The EtOAc layer was separated, dried with MgSO$_4$, filtered and adsorbed to silica and purified by silica gel flash column chromatography (15 minutes, 0-30% v/v EtOAc/hexanes) to produce pure 4-tert-butyl-1-((4-nitrophenyl)sulfonyl)piperidine (0.088 g, 0.27 mmol, 30% yield). $^1$H NMR (400 MHz, CDCl$_3$): δ 8.37 (d, J=8.9 Hz, 2H), 7.94 (d, J=8.9 Hz, 2H), 3.93-3.89 (m, 2H), 2.22 (td, J$_1$=12.2 Hz, J$_2$=2.4 Hz, 2H), 1.76-1.72 (m, 2H), 1.38 (qd, J$_1$=12.4 Hz, J$_2$=4.1 Hz, 2H), 0.89 (m, 1H), 0.82 (s, 9H).

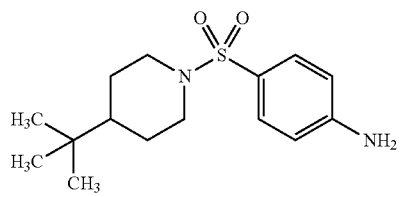 [SMILES: CC(C)(C)C1CCN(S(=O)(=O)c2ccc(N)cc2)CC1]

4-((4-tert-butylpiperidin-1-yl)sulfonyl)aniline. The 4-tert-butyl-1-((4-nitrophenyl)sulfonyl)piperidine (0.088 g, 0.27 mmol) was added to a vial and with MeOH:CH$_2$Cl$_2$ (3 mL:1 mL) and the reaction was cooled to 0° C. The Raney Nickel (0.002 g, 0.027 mmol) was added followed by portionwise addition of sodium borohydride (0.020 g, 0.54 mmol). The reaction stirred at 0° C. for 30 minutes and was then diluted with CH$_2$Cl$_2$ (10 mL) and filtered slowly. The CH$_2$Cl$_2$ layer was washed with water (10 mL), separated, dried with MgSO$_4$, filtered, adsorbed to silica and purified by silica gel flash column chromatography (15 minutes, 0-5% v/v MeOH/CH$_2$Cl$_2$) to produce pure 4-((4-tert-butylpiperidin-1-yl)sulfonyl)aniline (0.068 g, 0.23 mmol, 85% yield). $^1$H NMR (400 MHz, CDCl$_3$): δ 7.52 (d, J=8.7 Hz, 2H), 6.68 (d, J=8.7 Hz, 2H), 4.13 (s, 2H), 3.81-3.77 (m, 2H), 2.12 (td, J$_1$=12.2 Hz, J$_2$=2.4, 2H), 1.71-1.67 (m, 2H), 1.36 (qd, J$_1$=12.4, J$_2$=4.0 Hz, 4H), 0.87 (tt, J$_1$=12.2 Hz, J$_2$=3.3 Hz, 1H), 0.81 (s, 9H).

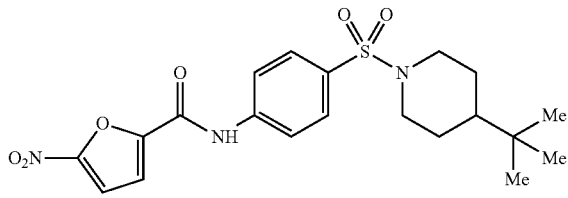 [SMILES: CC(C)(C)C1CCN(S(=O)(=O)c2ccc(NC(=O)c3ccc([N+](=O)[O-])o3)cc2)CC1]

N-(4-((4-tert-butylpiperidin-1-yl)sulfonyl)phenyl)-5-nitrofuran-2-carboxamide. To a microwave vial was added 4-((4-tert-butylpiperidin-1-yl)sulfonyl)aniline (0.068 g, 0.23 mmol), 5-nitro-2-furoyl chloride (0.037 g, 0.21 mmol) and acetonitrile (2 mL). The vial was sealed and heated to 150° C. in microwaves for 20 minutes. The reaction was then cooled to room temperature, diluted with CH$_2$Cl$_2$ (10 mL) and washed with saturated NaHCO$_3$ (10 mL). The CH$_2$Cl$_2$ layer was collected, dried with MgSO$_4$, filtered and adsorbed to silica gel. The crude product was purified by silica gel flash column chromatography (20 minutes, 0-5% v/v MeOH/CH$_2$Cl$_2$) to produce pure N-(4-((4-tert-butylpiperidin-1-yl)sulfonyl)phenyl)-5-nitrofuran-2-carboxamide (0.060 g, 0.138 mmol, 66% yield). $^1$H NMR (400 MHz, DMSO-d$_6$): δ 10.98 (s, 1H), 8.01 (d, J=8.9 Hz, 2H), 7.83 (d, J=4.0 Hz, 1H), 7.76 (d, J=8.8 Hz, 2H), 7.70 (d, J=4.0 Hz, 1H), 3.71 (d, J=11.6, 1H), 2.12 (t, J=11.8 Hz, 2H),1.67 (d, J=12.2 Hz, 2H), 1.19 (qd, J,=12.5 Hz, J$_2$=3.6 Hz, $^2$H), 0.91 (t, J=12.2 Hz, 1H), 0.78 (s, 9H). $^{13}$H NMR (125 MHz, DMSO-d0: 5 155.0, 152.0, 147.3, 142.0, 130.5, 128.7, 120.3, 117.3, 113.4, 54.9, 46.8, 44.8, 31.8, 27.0, 25.7. LCMS retention time: 3.517 min. LCMS Purity at 214 nm: 97.8%. HRMS: m/z calcd for C$_{20}$H$_{26}$N$_3$O$_6$S (M+H$^+$) 436.1537, found 436.1533. Melting point: 236-239° C.

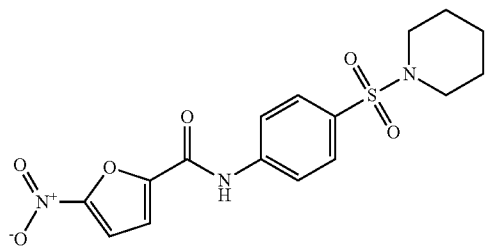

SID104222721
CID9415121
MLS003940501

N-(4-((piperidin-1-yl)sulfonyl)phenyl)-5-nitrofuran-2-carboxamide (SID 134228467; CID 9415121). To a microwave vial was added 4-((piperidin-1-yl)sulfonyl)aniline (0.13 g, 0.53 mmol), 5-nitro-2-furoyl chloride (0.10 g, 0.58 mmol) and acetonitrile (2 mL). The vial was sealed and heated to 150° C. in the microwave for 20 minutes. The reaction was cooled to room temperature and was diluted with CH$_2$Cl$_2$ (10 mL) and washed with saturated NaHCO$_3$ (10 mL). The CH$_2$Cl$_2$ layer was separated, dried with MgSO$_4$, filtered and adsorbed to silica gel. The crude product was purified by silica gel flash column chromatography (20 minutes, 0-5% v/v MeOH/CH$_2$Cl$_2$) to produce pure N-(4-((piperidin-1-yl)sulfonyl)phenyl)-5-nitrofuran-2$^-$carboxamide (0.17 g, 0.44 mmol, 82% yield). $^1$H NMR (400 MHz, DMSO-d$_6$): δ 10.99 (s, 1H), 8.01 (d, J=8.8 Hz, 2H), 7.84 (d, J=3.9 Hz, 1H), 7.76 (d, J=8.8 Hz, 2H), 7.71 (d, J=4.0 Hz, 1H), 2.88 (t, J=5.3, 4H), 1.55-1.53 (m, 4H), 1.37-1.35 (m, 2H). $^{13}$H NMR (125 MHz, DMSO-d$_6$): δ 155.0, 152.0, 147.3, 142.0, 130.5, 128.6, 120.4, 117.3, 113.4, 46.6, 24.7, 22.9. LCMS retention time: 3.131 min. LCMS Purity at 214 nm: 94.1%. HRMS: m/z calcd for C$_{16}$H$_{18}$N$_3$O$_6$S (M+H$^+$) 380.0911, found 390.0940. Melting point: 183-187° C.

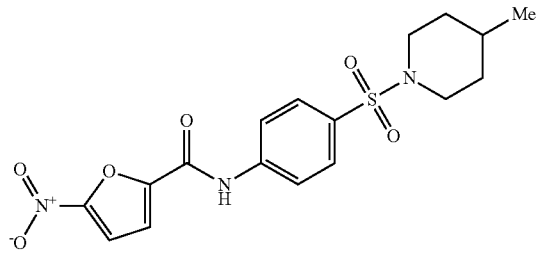

SID117695368
CID17146663
MLS003940500

N-(4-((4-methylpiperidin-1-yl)sulfonyl)phenyl)-5-nitrofuran-2-carboxamide (SID 134228466; CID 17146663). To a microwave vial was added 4-((4-methylpiperidin-1-yl)sulfonyl)aniline (0.11 g, 0.43 mmol), 5-nitro-2-furoyl chloride (0.082 g, 0.47 mmol) and acetonitrile (2 mL). The vial was sealed and heated to 150° C. in microwaves for 20 minutes. The reaction was then cooled to room temperature, diluted with CH$_2$Cl$_2$ (10 mL) and washed with saturated NaHCO$_3$ (10 mL). The CH$_2$Cl$_2$ layer was separated, dried with MgSO$_4$, filtered and adsorbed to silica gel. The crude product was purified by silica gel flash column chromatography (20 minutes, 0-5% v/v MeOH/CH$_2$Cl$_2$) to produce pure N-(4-((4-methylpiperidin-1-yl)sulfonyl)phenyl)-5-nitrofuran-2-carboxamide (0.14 g, 0.37 mmol, 86% yield). $^1$H NMR (400 MHz, DMSO-d$_6$): δ 10.99 (s, 1H), 8.01 (d, J=8.9 Hz, 2H), 7.83 (d, J=4.0 Hz, 1H), 7.76 (d, J=8.8 Hz, 2H), 7.71 (d, J=3.9 Hz, 1H), 3.59 (d, J=11.6 Hz, 2H), 2.19 (td, J,=11.8, J$_2$=2.2 Hz, 4H), 1.64 (d, J=10.8 Hz, 2H), 1.31-1.27 (m, 1H), 1.13 (qd, J$_1$=12.5 Hz, 3.6 Hz, 2H), 0.85 (d, J=6.4 Hz, 3H). $^{13}$H NMR (125 MHz, DMSO-d$_6$): δ 155.0, 152.0, 147.3, 142.0, 130.6, 128.6, 120.4, 117.3, 113.4, 46.1, 32.8, 29.3, 21.3. LCMS retention time: 3.184 min. LCMS Purity at 214 nm: 96.6%. HRMS: m/z calcd for C$_{17}$H$_{20}$N$_3$O$_6$S (M+H$^+$) 394.1067, found 394.1082. Melting point: 189-193° C.

EXAMPLE 11

Activity of ML291 Analogs

Five analogues of probe ML291 were prepared. All five compounds, including the probe, were synthesized and their associated data, along with the probe, are summarized in Table 9.

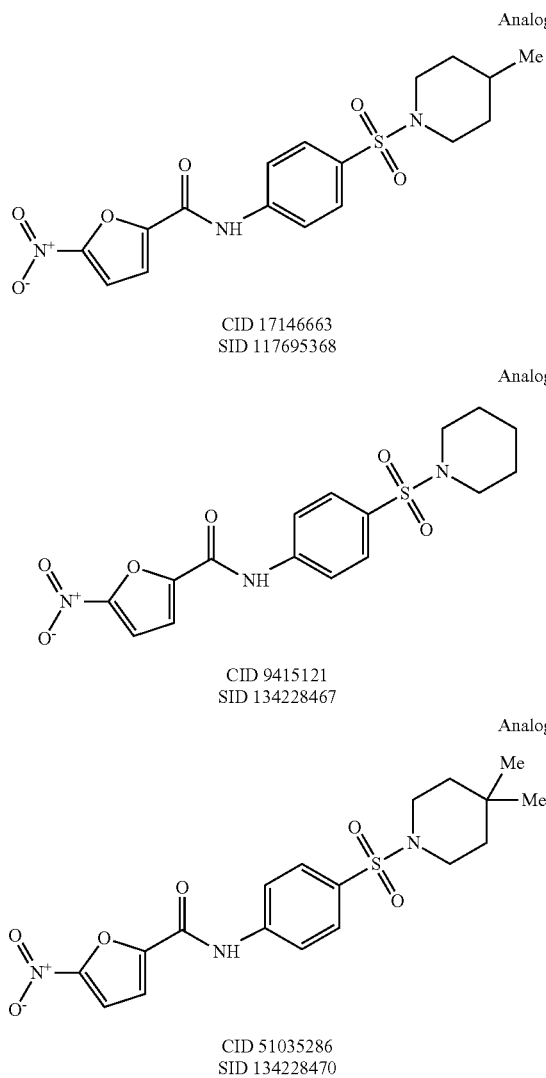

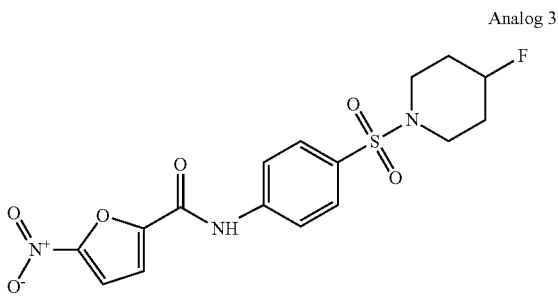

TABLE 9

| Compound | EC50 (μM) | | Amt (mg) |
|---|---|---|---|
| | UPR CHOP Assay[a] | UPR XBP1 Assay[a] | |
| ML291 | 0.78 | >80 | 21.1 |
| Analog 1 | 0.76 | >80 | 22.2 |
| Analog 2 | 0.74 | >80 | 23.2 |
| Analog 3 | 0.43 | >80 | 21.9 |
| Analog 4 | 0.65 | >80 | 22.5 |
| Analog 5 | 0.77 | >80 | 22.5 |

Data is an average of four runs (n = 4) for the UPR CHOP and UPR XBP assays.
[a]Conditions: F12 nutrient mix HAMs supplemented with 10% hi-FBS, 1X penicillin/streptomycin, 1X MEM-NEAA.

EXAMPLE 12

Additional ML291 Analogs

Additional analogs of ML291 are presented in Table 10.

TABLE 10

| Compound | PubChem SID | Structure |
|---|---|---|
| Analog 6 | 104222717 | 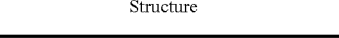 |

TABLE 10-continued
| Compound | PubChem SID | Structure |
|---|---|---|
| Analog 7 | 104222719 | 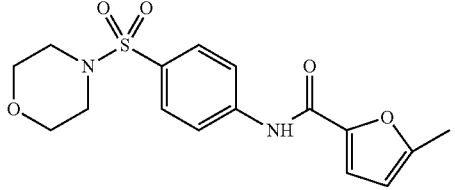 [SMILES: Cc1ccc(C(=O)Nc2ccc(S(=O)(=O)N3CCOCC3)cc2)o1] |
| Analog 8 | 104222721 | 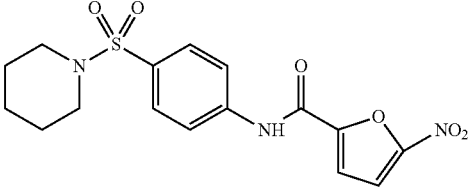 [SMILES: O=C(Nc1ccc(S(=O)(=O)N2CCCCC2)cc1)c1ccc([N+](=O)[O-])o1] |
| Analog 9 | 104222726 | 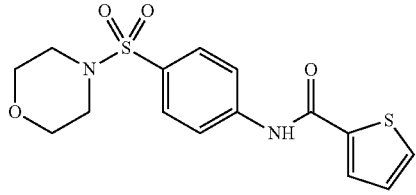 |
| Analog 10 | 104222727 | 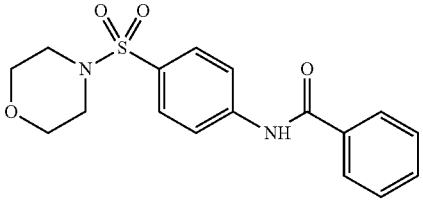 [SMILES: O=C(Nc1ccc(S(=O)(=O)N2CCOCC2)cc1)c1ccccc1] |
| Analog 11 | 104222728 | 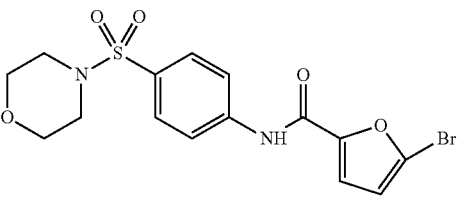 [SMILES: O=C(Nc1ccc(S(=O)(=O)N2CCOCC2)cc1)c1ccc(Br)o1] |
| Analog 12 | 104222729 | 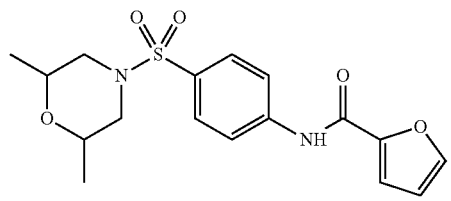 [SMILES: CC1CN(S(=O)(=O)c2ccc(NC(=O)c3ccco3)cc2)CC(C)O1] |
| Analog 13 | 104222730 | 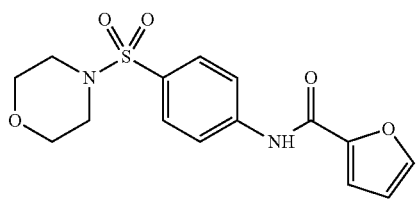 [SMILES: O=C(Nc1ccc(S(=O)(=O)N2CCOCC2)cc1)c1ccco1] |

TABLE 10-continued
| Compound | PubChem SID | Structure |
|---|---|---|
| Analog 14 | 104222731 | 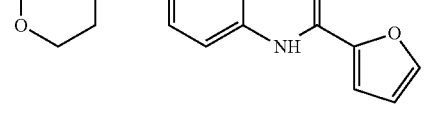 |
| Analog 15 | 104222733 | 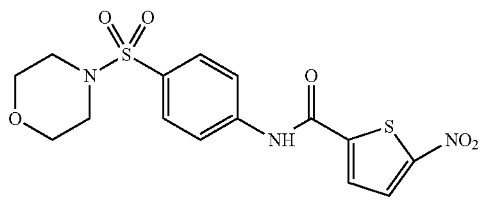 [SMILES: O=C(Nc1ccc(S(=O)(=O)N2CCOCC2)cc1)c1ccc([N+](=O)[O-])s1] |
| Analog 16 | 104222734 | 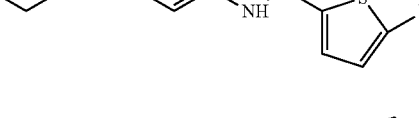 |
| Analog 17 | 117695369 | 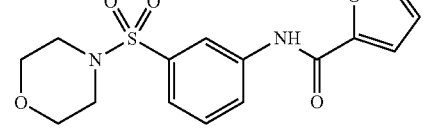 |
| Analog 18 | 117695370 | 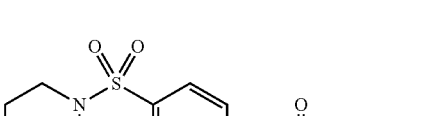 |
| Analog 19 | 117695371 | 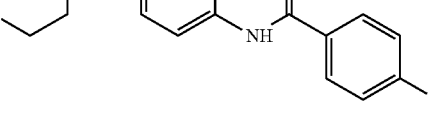 |
| Analog 20 | 117695372 | 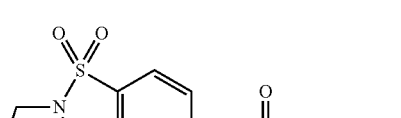 |

TABLE 10-continued

| Compound | PubChem SID | Structure |
| --- | --- | --- |
| Analog 21 | 117695373 | 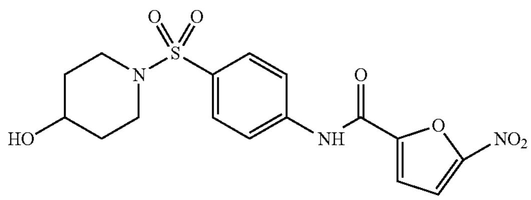 [SMILES: O=C(Nc1ccc(S(=O)(=O)N2CCC(O)CC2)cc1)c1ccc([N+](=O)[O-])o1] |
| Analog 22 | 117695374 | 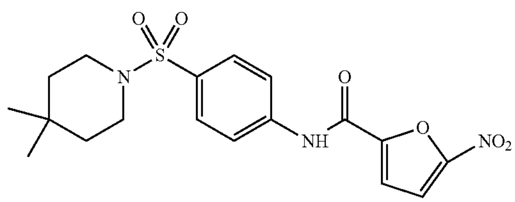 [SMILES: CC1(C)CCN(S(=O)(=O)c2ccc(NC(=O)c3ccc([N+](=O)[O-])o3)cc2)CC1] |
| Analog 23 | 117695375 | 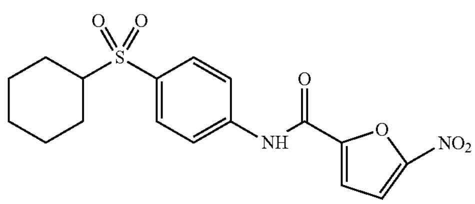 [SMILES: O=C(Nc1ccc(S(=O)(=O)C2CCCCC2)cc1)c1ccc([N+](=O)[O-])o1] |
| Analog 24 | — | 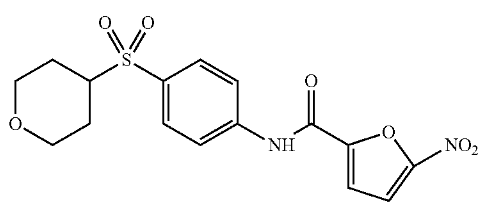 |
| Analog 25 | — | 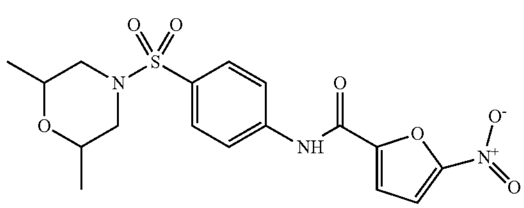 [SMILES: CC1CN(S(=O)(=O)c2ccc(NC(=O)c3ccc([N+](=O)[O-])o3)cc2)CC(C)O1] |
| Analog 26 | — | 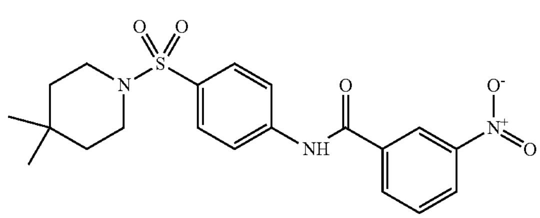 [SMILES: CC1(C)CCN(S(=O)(=O)c2ccc(NC(=O)c3cccc([N+](=O)[O-])c3)cc2)CC1] |
| Analog 27 | — | 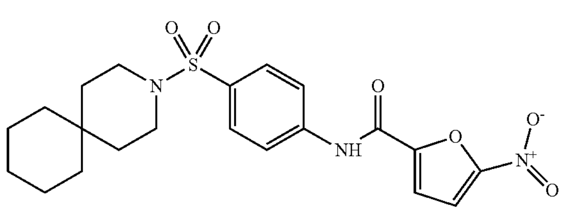 [SMILES: O=C(Nc1ccc(S(=O)(=O)N2CCC3(CCCCC3)CC2)cc1)c1ccc([N+](=O)[O-])o1] |

TABLE 10-continued

| Compound | PubChem SID | Structure |
|---|---|---|
| Analog 28 | — | 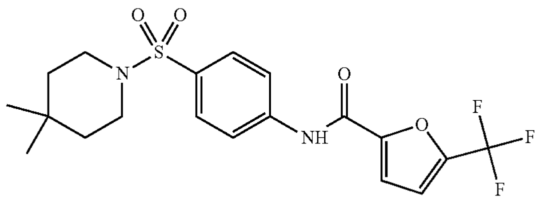 [SMILES: CC1(C)CCN(S(=O)(=O)c2ccc(NC(=O)c3ccc(C(F)(F)F)o3)cc2)CC1] |
| Analog 29 | — | 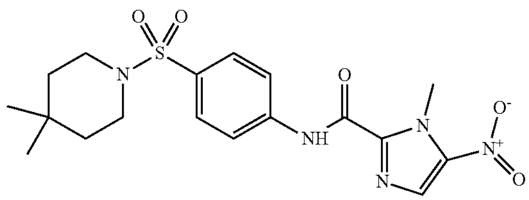 [SMILES: Cn1c([N+](=O)[O-])cnc1C(=O)Nc1ccc(S(=O)(=O)N2CCC(C)(C)CC2)cc1] |
| Analog 30 | — | 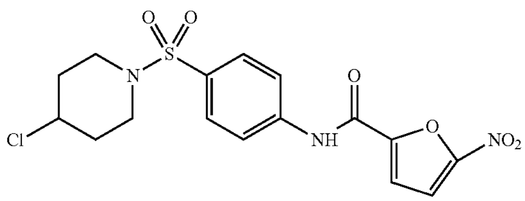 [SMILES: O=C(Nc1ccc(S(=O)(=O)N2CCC(Cl)CC2)cc1)c1ccc([N+](=O)[O-])o1] |

To further enhance potency and efficacy, lead optimization studies are carried out, wherein common nitro group isosteres such as nitrile and carboxylic acid groups, along with pyridine derivatives are prepared, which have been reported as successful surrogates for aryl nitro functionality (Meanwell (2011) *J. Med. Chem.* 54:2529-2591). Additionally, the nitro could be replaced with ester or sulfonamide, sulfone, an approach that was very successful in the development of the BCL2 inhibitor ABT-263 (Oltersdorf, et al. (2005) *Nature* 435:677-681).

What is claimed is:

1. A method of treating an oral squamous cell carcinoma, ovarian cancer or leukemia, in a subject comprising administering to a subject in need of treatment, a pharmaceutical composition comprising the compound:

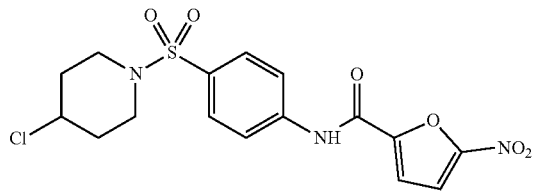 [SMILES: O=C(Nc1ccc(S(=O)(=O)N2CCC(Cl)CC2)cc1)c1ccc([N+](=O)[O-])o1]

thereby treating the subject's oral squamous cell carcinoma, ovarian cancer or leukemia.

* * * * *